(12) United States Patent
Wolf, II

(10) Patent No.: US 9,132,273 B2
(45) Date of Patent: Sep. 15, 2015

(54) APPARATUS AND METHOD USING NEAR INFRARED REFLECTOMETRY TO REDUCE THE EFFECT OF POSITIONAL CHANGES DURING SPINAL CORD STIMULATION

(71) Applicant: Erich W. Wolf, II, Lake Charles, LA (US)

(72) Inventor: Erich W. Wolf, II, Lake Charles, LA (US)

(*) Notice: Subject to any disclaimer, the term of this patent is extended or adjusted under 35 U.S.C. 154(b) by 138 days.

(21) Appl. No.: 13/780,470

(22) Filed: Feb. 28, 2013

(65) Prior Publication Data

US 2014/0074182 A1    Mar. 13, 2014

Related U.S. Application Data

(63) Continuation-in-part of application No. 13/567,966, filed on Aug. 6, 2012, now Pat. No. 8,543,213, which is a continuation of application No. 12/925,231, filed on Oct. 14, 2010, now Pat. No. 8,239,038.

(51) Int. Cl.
*A61N 1/36* (2006.01)
*G01N 21/359* (2014.01)
(Continued)

(52) U.S. Cl.
CPC .......... *A61N 1/36139* (2013.01); *A61B 5/1116* (2013.01); *A61N 1/0551* (2013.01); *A61N 1/36071* (2013.01); *A61N 1/36157* (2013.01); *G01N 21/359* (2013.01); *A61B 5/407* (2013.01); *A61B 5/4836* (2013.01);
(Continued)

(58) Field of Classification Search
CPC ............. A61N 1/36139; A61N 1/0551; A61B 5/1116; A61B 5/047

USPC ...................................... 607/46, 62, 116, 117
See application file for complete search history.

(56) References Cited

U.S. PATENT DOCUMENTS

| 5,556,421 A | 9/1996 | Prutchi et al. |
| 5,824,021 A | 10/1998 | Rise |

(Continued)

FOREIGN PATENT DOCUMENTS

WO    2007059362    5/2007

OTHER PUBLICATIONS

Philip, Geo M., et al., Fabrication of Negative Micro Axicons in Optical Fibers via Chemical Etching, ICOP 2009—International Conference on Optics and Photonics, Oct. 30, 2009, CSIO, Chandigarh, India.

(Continued)

*Primary Examiner* — George Evanisko
(74) *Attorney, Agent, or Firm* — Schultz & Associates, P.C.

(57) ABSTRACT

A positionally sensitive spinal cord stimulation apparatus and method using near-infrared (NIR) reflectometry are provided for automatic adjustments of spinal cord stimulation. The system comprises an electrode assembly with an integrated optical fiber sensor for sensing spinal cord position. The integrated optical fiber sensor, comprising a set of optical elements for emitting light from a set of IR emitters and for collecting reflected light into a set of IR photodetectors, determines a set of measured optical intensities. As the spinal cord changes position, the angles of incidence for light from the IR emitter and the measured optical intensities change. A ratio of measured optical intensities in combination with a total measured optical intensity is used to interpolate a set of electrode stimulation settings from a calibration table. Electrode pulse characteristics are adjusted in real time to minimize changes in stimulation perceived by the patient during motion.

19 Claims, 24 Drawing Sheets

(51) Int. Cl.
  *A61B 5/11* (2006.01)
  *A61N 1/05* (2006.01)
  *A61N 1/372* (2006.01)
  *G06F 19/00* (2011.01)
  *A61B 5/00* (2006.01)

(52) U.S. Cl.
  CPC .... *A61B 2562/0233* (2013.01); *A61N 1/36171* (2013.01); *A61N 1/36175* (2013.01); *A61N 1/37252* (2013.01); *G06F 19/3412* (2013.01); *G06F 19/3481* (2013.01)

(56) References Cited

U.S. PATENT DOCUMENTS

| | | | |
|---|---|---|---|
| 6,058,331 | A | 5/2000 | King |
| 6,120,467 | A | 9/2000 | Schallhorn |
| 6,169,924 | B1 | 1/2001 | Meloy et al. |
| 6,587,724 | B2 | 7/2003 | Mann |
| 6,622,048 | B1 | 9/2003 | Mann et al. |
| 6,871,099 | B1 | 3/2005 | Whitehurst et al. |
| 6,937,882 | B2 | 8/2005 | Steuer et al. |
| 7,127,296 | B2 | 10/2006 | Bradley |
| 7,162,304 | B1 | 1/2007 | Bradley |
| 7,216,000 | B2 | 5/2007 | Sieracki et al. |
| 7,263,402 | B2 | 8/2007 | Thacker |
| 7,330,762 | B2 | 2/2008 | Boveja |
| 7,333,857 | B2 | 2/2008 | Campbell |
| 7,359,751 | B1 | 4/2008 | Erickson et al. |
| 7,463,927 | B1 | 12/2008 | Chaouat |
| 7,539,543 | B2 | 5/2009 | Schiff et al. |
| 7,650,190 | B2 | 1/2010 | Zhou et al. |
| 7,684,869 | B2 | 3/2010 | Bradley et al. |
| 7,801,621 | B1 | 9/2010 | Thacker et al. |
| 7,805,197 | B2 | 9/2010 | Bradley |
| 8,165,676 | B2 * | 4/2012 | Donofrio .................... 607/19 |
| 2003/0153959 | A1 | 8/2003 | Thacker et al. |
| 2005/0096720 | A1* | 5/2005 | Sharma et al. ............. 607/122 |
| 2005/0222628 | A1 | 10/2005 | Krakousky |
| 2006/0217793 | A1* | 9/2006 | Costello .................... 607/122 |
| 2007/0027514 | A1 | 2/2007 | Gerber |
| 2007/0100398 | A1 | 5/2007 | Sloan |
| 2009/0118787 | A1 | 5/2009 | Moffitt et al. |
| 2009/0270960 | A1 | 10/2009 | Zhao et al. |
| 2010/0022861 | A1 | 1/2010 | Cinbis et al. |
| 2010/0105997 | A1 | 4/2010 | Ecker et al. |
| 2010/0106220 | A1 | 4/2010 | Ecker et al. |

OTHER PUBLICATIONS

Utzinger, Urs, et al., Fiber Optic Probes for Biomedical Optical Spectroscopy, Feb. 2001, Tucson, Arizona.
Scott Prahl, Tabulated Molar Extinction Coefficient for Hemoglobin in Water, http://omlc.ogi.edu/spectra/hemoglobin/summary.html, Mar. 4, 1998, pp. 1-7.
Urs Utzinger, Oxygen saturation, http://www2.engr.arizona.edu/~bme517/supporting%20documents/PulseOximeter/Pulse%20Oxi%20Meter%20Laboratory.htm#_Toc67647950, 2002, pp. 1-24.

* cited by examiner

FRONT, 0°

RIGHT, 90°

BACK, 180°

LEFT, 270°

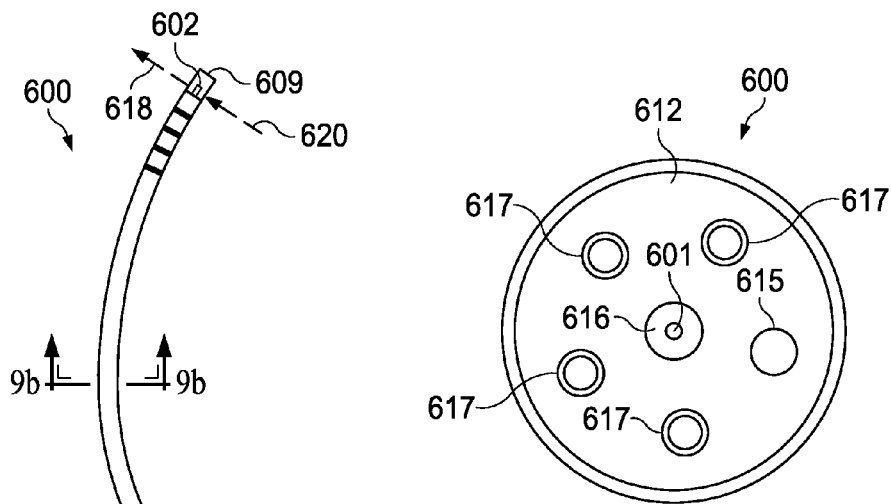
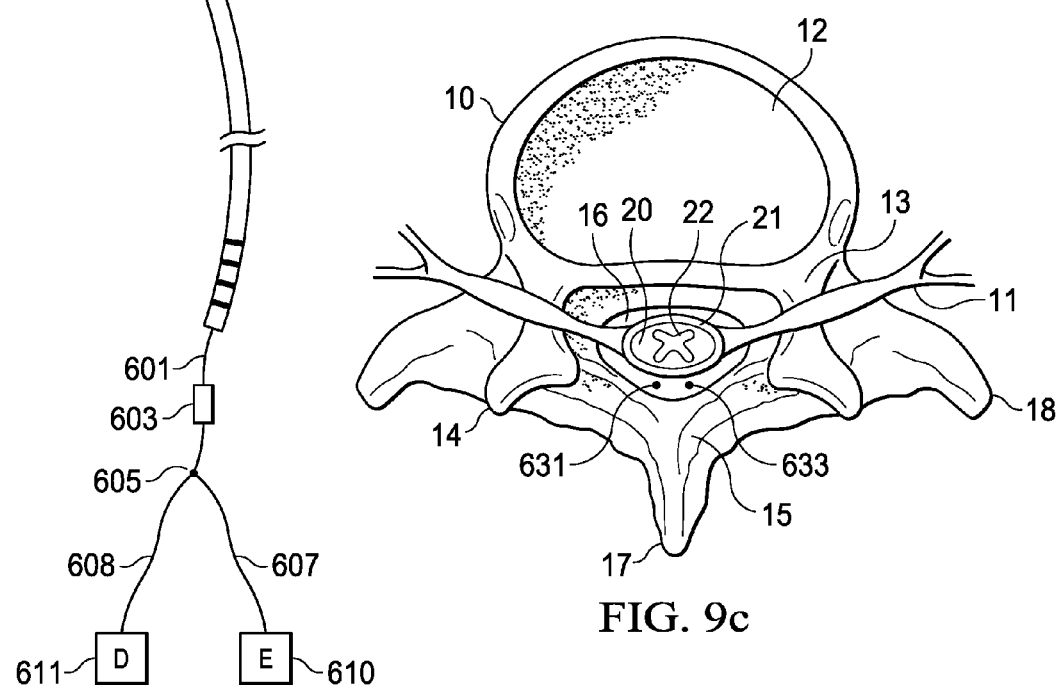
FIG. 9b
FIG. 9c
FIG. 9a

FRONT, 0°

RIGHT, 90°

BACK CLOSE, 180°

LEFT, 270°

APPARATUS AND METHOD USING NEAR INFRARED REFLECTOMETRY TO REDUCE THE EFFECT OF POSITIONAL CHANGES DURING SPINAL CORD STIMULATION

CROSS-REFERENCE TO RELATED APPLICATIONS

This application is a Continuation-in-Part application claiming priority benefit from U.S. patent application Ser. No. 13/567,966, filed on Aug. 6, 2012, which is continuation of U.S. patent application Ser. No. 12/925,231, filed on Oct. 14, 2010, now U.S. Pat. No. 8,239,038.

FIELD OF INVENTION

This invention relates generally to spinal cord stimulation (SCS) and technique for automatic adjustments of SCS using near-infrared (NIR) reflectometry.

BACKGROUND

Spinal cord stimulation is a technique which uses an implanted electrode array to control chronic pain. The electrode array is typically implanted in a fixed position within the epidural space near the spinal cord. A signal generator delivers current pulses to the spinal cord via the implanted electrode array. The current pulses induce parasthesiae which help block the perception of pain.

In FIG. 1, spinal column 1 is shown to have a number of vertebrae, categorized into four sections or types: lumbar vertebrae 2, thoracic vertebrae 3, cervical vertebrae 4 and sacral vertebrae 5. Cervical vertebrae 4 include the 1st cervical vertebra (C1) through the 7th cervical vertebra (C7). Just below the 7th cervical vertebra is the first of twelve thoracic vertebrae 3 including the 1st thoracic vertebra (T1) through the 12th thoracic vertebra (T12). Just below the 12th thoracic vertebrae 3, are five lumbar vertebrae 2 including the 1st lumbar vertebra (L1) through the 5th lumbar vertebra (L5), the 5th lumbar vertebra being attached to sacral vertebrae 5 (S1 to S5), sacral vertebrae 5 being naturally fused together in the adult.

In FIG. 2, representative thoracic vertebra 10 is shown to have a number of notable features which are in general shared with lumbar vertebrae 2 and cervical vertebrae 4. The thick oval segment of bone forming the anterior aspect of vertebra 10 is vertebral body 12. Vertebral body 12 is attached to bony vertebral arch 13 through which spinal nerves 11 run. Vertebral arch 13, forming the posterior of vertebra 10, is comprised of two pedicles 14, which are short stout processes that extend from the sides of vertebral body 12 and bilateral laminae 15. The broad flat plates that project from pedicles 14 join in a triangle to form a hollow archway, spinal canal 16. Spinous process 17 protrudes from the junction of bilateral laminae 15. Transverse processes 18 project from the junction of pedicles 14 and bilateral laminae 15. The structures of the vertebral arch protect spinal cord 20 and spinal nerves 11 that run through the spinal canal.

Surrounding spinal cord 20 is dura 21 that contains cerebrospinal fluid (CSF) 22. Epidural space 24 is the outermost part of the spinal canal. It is the space within the spinal canal formed by the surrounding vertebrae lying outside the dura.

Referring to FIGS. 1, 2 and 3, the placement of an electrode array for spinal cord stimulation according to the prior art is shown. Electrode array 30 is positioned in epidural space 24 between dura 21 and the walls of spinal canal 16 towards the dorsal aspect of the spinal canal nearest bilateral laminae 15 and spinous process 17.

FIG. 4 shows a prior art electrode array 30 including a set of electrode contacts 35 sealed into elastomeric housing 36. Electrode array 30 has a set of electrode leads 31 which are connected to electrical pulse generator 32 and controller 33. The electrical pulse generator may be outside of the body or it may be implanted subcutaneously. Each electrode contact has a separate electrical conductor in the set of electrode leads 31 so that the current to each contact may be independently conducted and controlled.

The anatomical distribution of parasthesiae is dependent upon the spatial relationship between a stimulating electric field generated by the electrode array and the neuronal pathways within the spinal cord. The distribution may be changed by altering the current across one or more electrodes of the electrode array. Changing anode and cathode configurations of the electrode array also alters the distribution and hence, the anatomical pattern of the induced parasthesiae.

Proper intensity of the current pulses is important. Excessive current produces an uncomfortable sensation. Insufficient current produces inadequate pain relief. Body motion, particularly bending and twisting, causes undesired and uncomfortable changes in stimulation due to motion of the spinal cord relative to the implanted electrode array.

There are methods and systems for controlling implanted devices within the human body. For example, Ecker et al, in U.S. Patent Application No. 2010/0105997, discloses an implantable medical device that includes a controller and a plurality of sensor modules. A sensor includes at least one light source that emits light at a particular wavelength, which scatters through blood-perfused tissue a detector senses the light reflected by blood mass of a patient.

U.S. Pat. No. 7,684,869 to Bradley, et al. discloses a system using an interelectrode impedance to determine the relative orientation of a lead other leads in the spinal column. Bradley et al. further disclose that interelectrode impedance may be used to adjust stimulation energy.

U.S. Patent Application No. 2009/0118787 to Moffitt, et al. discloses electrical energy conveyed between electrodes to create a stimulation region. Physiological information from the patient is acquired and analyzed to locate a locus of the stimulation region. The stimulation region is electronically displaced.

Deficiencies exist in the prior art related to accuracy of spinal cord stimulation in relieving pain under changing circumstances. The deficiencies are most pronounced while the patient is moving. The prior art does not provide a satisfactory way to automatically adjust spinal cord stimulation to compensate for motion between the electrodes and the spinal cord to maintain a constant level of pain relief during patient motion.

SUMMARY OF PREFERRED EMBODIMENTS

Embodiments of the present invention operate to automatically adjust spinal cord stimulation to compensate for patient movement. Automatic adjustment results in consistent parasthesiae and conservation of battery power.

The disclosure demonstrates a novel optical sensor, generally useful in many fields of endeavor, in which a probe light beam is emitted from the sensor and a responsive light beam is collected by the sensor, where the sensor comprises a negative axicon element coupled to an optical fiber. In a preferred embodiment, the negative axicon is embedded in the end of the optical fiber.

The optical fiber is further coupled to an active optical element which can be an optical emitter or an optical detector. In a preferred embodiment, both an optical emitter and an optical detector are coupled to a single optical fiber with the negative axicon using an optical circulator. In another preferred embodiment, an optical isolator can be employed.

Disclosed is a stimulator system comprising a controller, a set of optical emitters operatively connected to the controller, generating a set of emitted light beams. A set of optical detectors are operatively connected to the controller, receiving a set of reflected light beams. A set of optical elements are operatively coupled to the set of optical emitters and to the set of optical detectors, emitting the set of emitted light beams and collecting the set of reflected light beams. A set of electrodes are operatively connected to the controller and the controller directs a set of currents to the set of electrodes based on the set of reflected light beams.

In an aspect of the system, the set of electrodes are adjacent the set of optical elements.

In another aspect of the system, an optical fiber is coupled to an optical emitter and further coupled to an optical detector in the set of optical detectors. The optical fiber is further coupled to an optical element in the set of optical elements.

In an embodiment of the system, the system comprises an implantable lead encasing the optical fiber and a lumen wherein the implantable lead further comprises an EMI shield. In a related aspect, the implantable lead further comprises carbon nanotubes.

In another aspect of the system an optical circulator is operatively coupled to the optical emitter, the optical detector and the optical fiber.

A preferred embodiment is conceived wherein an optical element in the set of optical elements further comprises a negative axicon. Further to the preferred embodiment, the negative axicon subtends an angle less than twice the complement of the critical angle for the light emitted from the optical fiber. In an alternate embodiment, a reflective coating is applied to the negative axicon.

In an alternate embodiment, an optical element in the set of optical elements further comprises a beveled surface. The beveled surface can comprise a reflective surface and in another aspect the reflective surface is positioned at an angle less than the complement of the critical angle for the light emitted from the optical fiber.

In another embodiment, an optical element in the set of optical elements further comprises a lens.

In an aspect of the system, the controller derives a set of current amplitudes for the set of currents based on an interpolation of a set of calibrated current amplitudes.

In another aspect of the system, the controller derives a set of current amplitudes for the set of currents based on time averaging of a set of historical current amplitudes.

In yet another aspect of the system, the controller derives a set of current pulse widths for the set of currents based on at least one of the group consisting of time averaging a set of current pulse widths, time averaging a set of current amplitudes, interpolating the set of current pulse widths and interpolating the set of current amplitudes.

In yet another aspect of the system, the controller derives a set of current pulse frequencies for the set of currents based on at least one of the group consisting of time averaging a set of current pulse frequencies, time averaging a set of current amplitudes, interpolating the set of current pulse frequencies and interpolating the set of current amplitudes.

In a preferred embodiment, the system further comprises a calibration unit operatively connected to the controller for calibrating the set of current pulse amplitudes, pulse widths and pulse frequencies.

BRIEF DESCRIPTION OF DRAWINGS

The following disclosure is understood best in association with the accompanying figures. Like components share like numbers.

FIG. 6c shows a cross-section of a stimulator lead along line 6c-6c from FIG. 6a.

FIG. 9a shows an alternate embodiment of a stimulator lead having a single optical fiber operating as an optical emitter and an optical collector.

FIG. 9b shows a cross-section of an alternate embodiment of a stimulator lead along line 9b-9b from FIG. 9a.

FIG. 9c shows placement of a set of stimulator leads.

DETAILED DESCRIPTION

Figure 1:
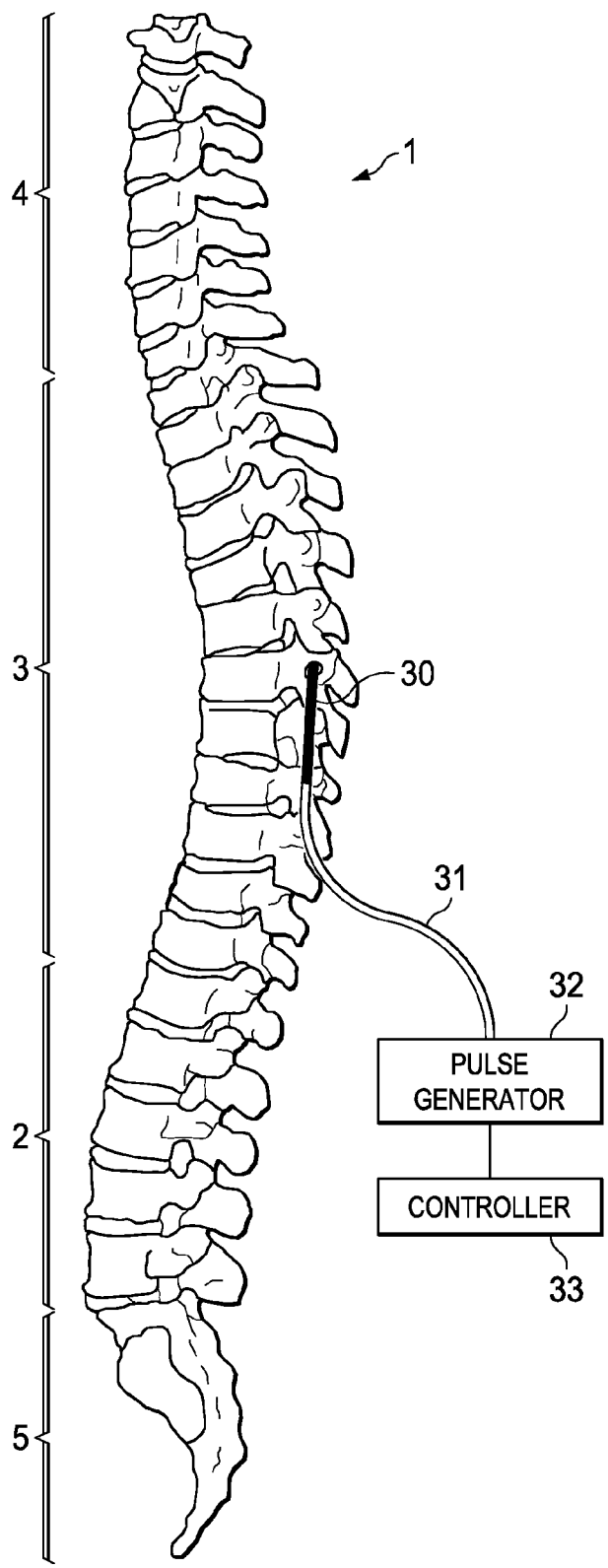
FIG. 1 shows a view of the human spine showing the various types of vertebrae and an approximate position of an electrode array for spinal cord stimulation.
Figure 4:
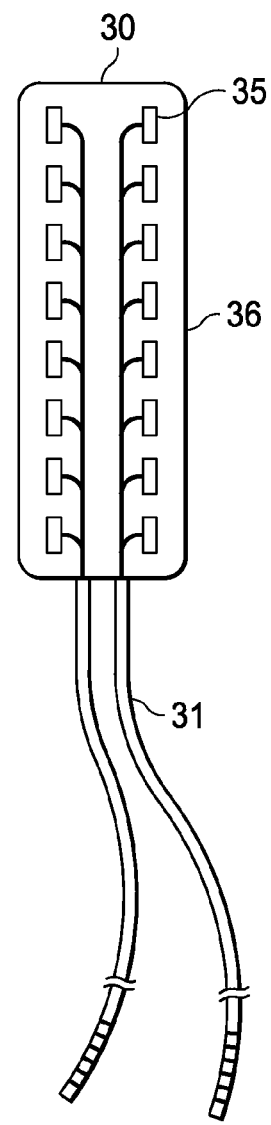
FIG. 4 shows a prior art electrode array for spinal cord stimulation.
Figure 2:
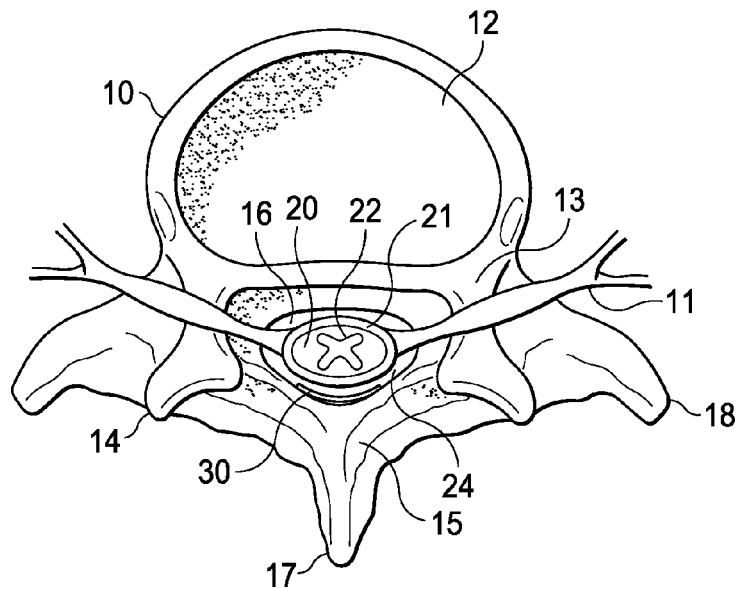
FIG. 2 shows an axial view of a thoracic vertebra indicating the position of the spinal cord and an electrode array for spinal cord stimulation.
Figure 3:
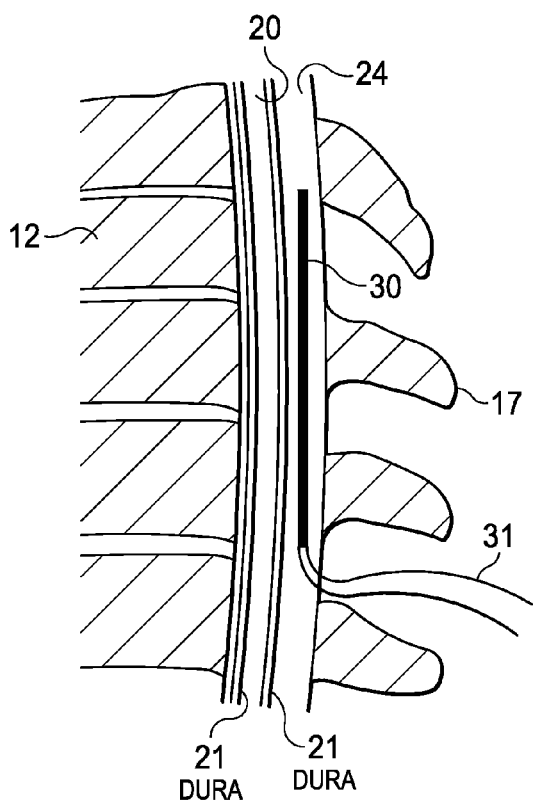
FIG. 3 shows a sagital cross section view of the human spine showing the approximate position of an electrode array for spinal cord stimulation.

The distance between a stimulating electrode and the spinal cord surface may be inferred from a function dependent upon: 1) the optical path lengths of light between a near infrared light emitter and a set of optical detectors, where the light is reflected from the spinal cord; 2) the spinal cord geometry; 3) the optical divergence of the light emitter; and 4) the presence of chromophores in the optical path.

The dura surrounding the spinal cord itself is translucent to near infrared light. Near infrared light will be scattered by, and will reflect from, the spinal cord. Cerebrospinal fluid (CSF) will negligibly scatter near infrared light and will not act as a significant reflector of near-infrared light. Light from the light emitter passes through the thin, relatively avascular dura to enter the CSF. Light incident on the spinal cord experiences scatter resulting in a portion being reflected and another portion being absorbed by chromophores.

Optical absorption in a fluid medium may be described by the Beer-Lambert Law (Beer's Law), which is reasonably accurate for a range of chromophores and concentrations. Beer's Law states that the optical absorbance of a fluid with a chromophore concentration varies linearly with path length through the fluid and the chromophore concentration as:

$$A_\lambda = \epsilon_\lambda bc, \quad (1)$$

where:
$\epsilon_\lambda$ = molar absorptivity or extinction coefficient of the chromophore at wavelength $\lambda$ (the optical density of a 1-cm thick sample of a 1 M solution);
b = sample path length in centimeters; and
c = concentration of the compound in the sample, in molarity (mol L$^{-1}$).

The absorbance ($A_\lambda$) at a wavelength $\lambda$ is related to the ratio of light energy passing through the fluid, I, to the incident light energy, $I_0$, in $$A_\lambda = -\log(I/I_0). \quad (2)$$

For deoxyhemoglobin and oxyhemoglobin, the extinction coefficient spectra are well known.

The path length within the spinal cord is dependent upon the geometry of the ellipsoid shaped spinal cord and its normal vector relative to the optical axes of the emitter and detector pair.

The optical path length within CSF is roughly equal to the nominal geometric path length as the scatter is small and the index of refraction does not vary considerably along the path. Light absorption of the CSF may be approximated by that of its primary constituent, $H_2O$. Sensitivity of the system to CSF path length may be optimized using a light wavelength at a local maxima of the water extinction coefficient curve near 950-1100 nm.

When considering the light emitter wavelength, one must also consider the extinction coefficients of the primary chromophores, deoxy- and oxy-hemoglobin. To minimize effects of blood flow changes within the spinal cord (although these are thought to be insignificant in the quasi-static sense), one may select the isosbestic wavelength of these chromophore species, preferably at about 805 nm.

The geometry of the light emitter and detector aperture relative to the spinal cord is the parameter most prone to variability. The variance results from factors such as dependence upon placement of the electrode within the spinal canal, canal diameter, spinal cord shape, spinal cord caliber, and presence of scoliotic or kyphotic curvature within the spine. Consequently, this geometric parameter is the primary reason that the system must be calibrated, in situ, in vivo. Spinal cord position may then be inferred through various methods from data obtained at extremes of body position.

The effects of geometry may be minimized by minimizing the angle between the light emitter and optical detector optical axes relative to the spinal cord surface normal vector.

The beam divergence of the light emitter relative to the incident and reflected rays will influence the detected light amplitude.

It is desirable to maintain a constant electric field at a group of target cells in the spinal cord as the spinal cord moves in order to consistently reduce the transmission of a pain sensation to the brain. As the patient bends forward towards a 0° direction, the spinal cord moves forward within its orbit in the spinal canal. An equal increase in stimulation pulse amplitude for each electrode pair is required to maintain the same electric field density. As the patient bends to the right towards a 90° direction, the spinal cord moves to the right within its orbit in the spinal canal. A decrease in electrode stimulation pulse amplitude in the right electrode and an increase in electrode stimulation pulse amplitude in the left electrode of the electrode pair is required. As the patient bends backward towards a 180° direction, the spinal cord moves back within its orbit within the spinal canal. A decrease in electrode stimulation pulse amplitude is required to maintain a constant electric field across the spinal cord. As the patient bends to the left towards a 270° direction, the spinal cord moves to the left within its orbit. A decrease in electrode stimulation pulse amplitude in the left electrode and an increase in electrode stimulation pulse amplitude in the right electrode of the electrode pair is required.

Figure 5A:
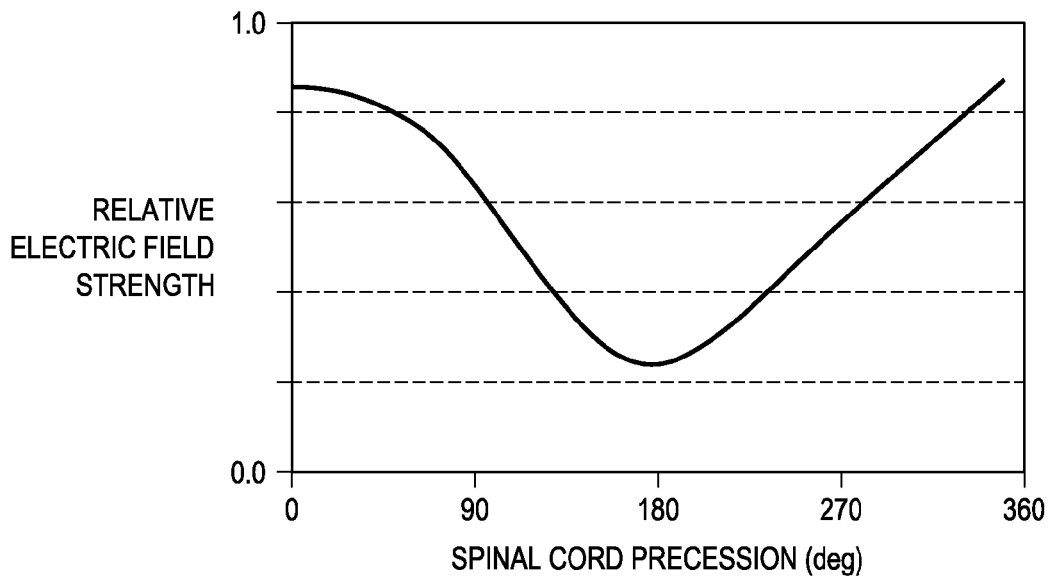
FIGS. 5a and 5b show the relative electric field produced by a preferred embodiment as the spinal cord precesses about an orbit within the spinal canal.
Figure 5B:
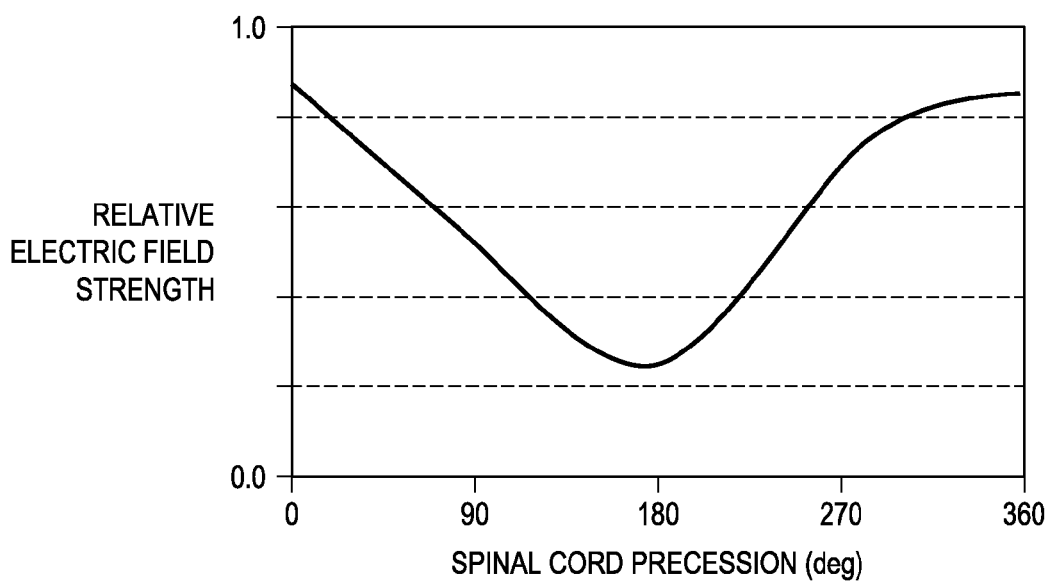

FIGS. 5a and 5b show the relative electric field intensity required to be generated at a left and right electrode, respectively, for maintenance of a constant field at any point across in a horizontal cross section of the spinal cord as the spinal cord is moved through an orbit of 360° in the spinal canal.

Figure 6A:
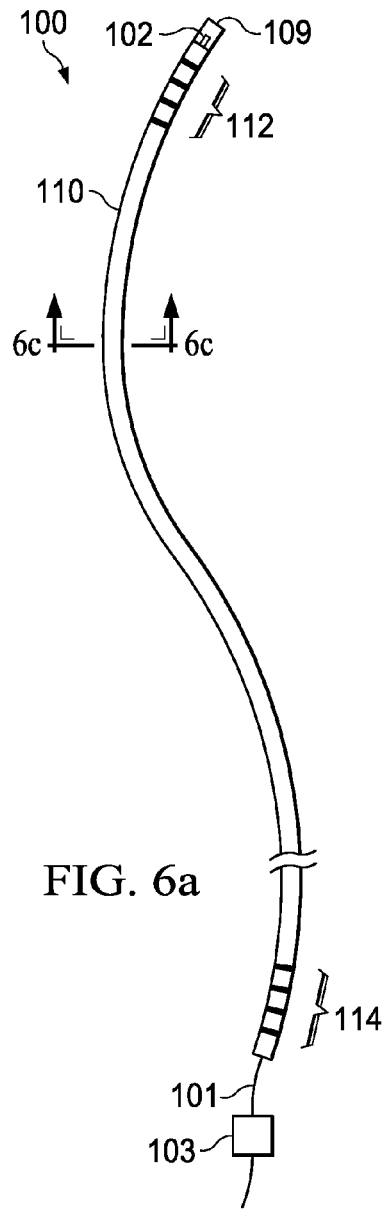
FIGS. 6a and 6b show a stimulator lead for spinal cord stimulation incorporating an optical fiber.
Figure 6C:
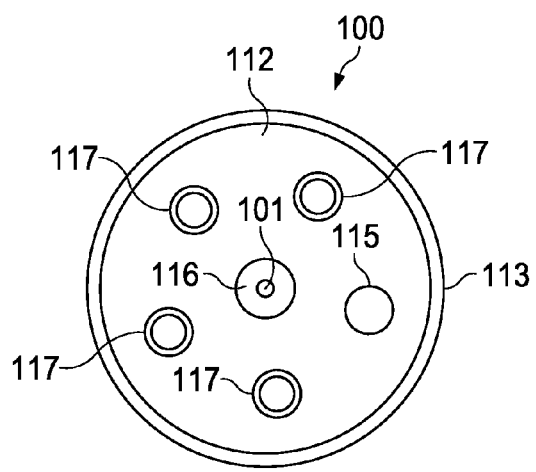
Figure 6B:
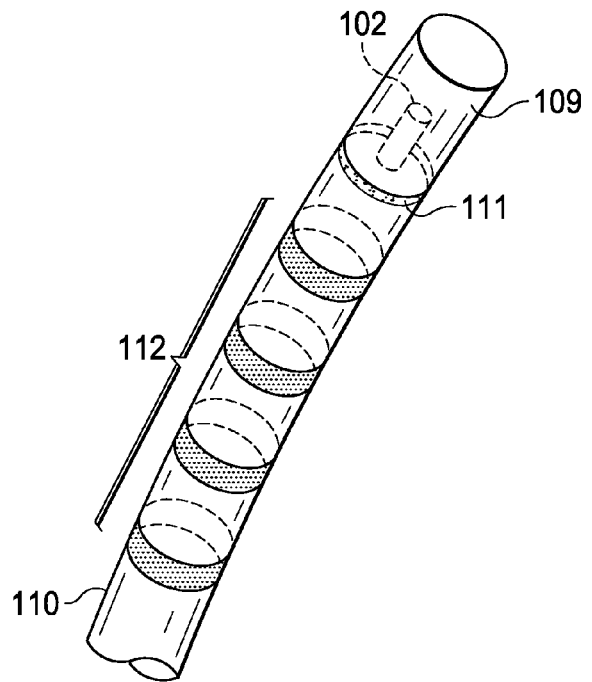

Referring to FIGS. 6a and 6b, a preferred embodiment stimulator lead 100 is shown. Stimulator lead 100 includes a set of stimulator electrodes 112 at a distal end electrically connected through lead cable 110 to a proximal set of electrode contacts 114 at a proximal end. The set of stimulator electrodes and the set of proximal electrode contacts are preferably annular and integrated into the lead cable. Stimulator lead 100 further includes optical fiber 101 having distal optical element 102 at the distal end and fiber optic connector 103 at the proximate end. Distal optical element 102 is configured as an optical emitter, an optical collector or as a combination of optical emitter and collector. Distal optical element 102 extends into cap 109. In a preferred embodiment, cap 109 is an extension of lead cable 110 which is sealed at the distal tip. In an alternate embodiment, cap 109 is a transparent hollow cylinder and bonded to lead cable 110 with adhesive at 111. Cap 109 is preferably comprised of glass or plastic and may contain an index matching fluid.

In an alternate embodiment, cap 109 can be comprised of a solid cylinder formed in place around distal optical element 102. In this embodiment, the cylinder is not hollow and is comprised of a transparent plastic such as Lexan™.

Referring to FIG. 6c, a cross-section of lead cable 110 is shown. Lead cable 110 comprises a sheathed outer surface 113 which encapsulates electrode leads 117, lumen 115 and lumen 116 in filler material 112. Lumen 116 encloses optical fiber 101. Lumen 115 provides a hollow cavity for a wire stylet to be inserted into the lead cable for the purpose of directing the position of the lead cable while being inserted into the epidural space of a patient. In a preferred embodiment lumen 116 is centrally located in the electrode lead while lumen 115 is positioned off axis. In alternate embodiments, lumen 115 is centrally located. In other alternate embodiments, lumen 116 and lumen 115 are incorporated into a single lumen in which the wire stylet is initially placed for insertion of the lead cable. The wire stylet is removed after insertion of the lead cable and optical fiber 101 is then threaded into the single lumen.

In a preferred embodiment, sheathed outer surface 113 includes an EMI shield. Filler material 112 preferably includes a polyimide polymer. Filler material 112 can also include additional materials with physical properties that enhance the EMI shielding capability of lead cable 110.

In an alternate embodiment, filler material 112 may include a carbon nano-tube composite such as that disclosed in U.S. Pat. No. 7,413,474 to Liu, et al. The disclosure of U.S. Pat. No. 7,413,474 is incorporated herein by reference.

Figure 6D:
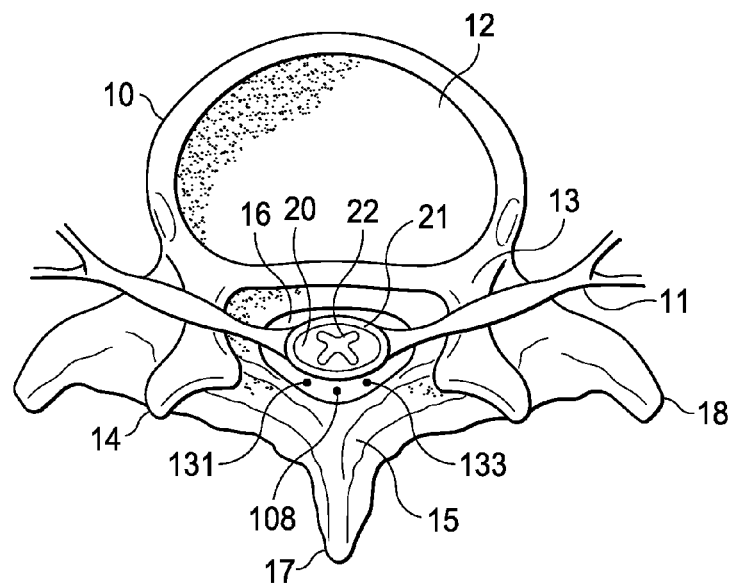
FIG. 6d shows placement of a set of stimulator leads.

Referring to FIG. 6d, placement of a set of stimulator leads is shown. The stimulator leads are positioned in the epidural space between the dura and the walls of the spinal canal. In a preferred embodiment, optical emitter 108 is situated between optical collectors 131 and 133.

FIGS. 7a-7e show suitable optical configurations for a distal optical element disposed on an optical fiber of a stimulator lead. FIGS. 7a-7e are intended as examples and should not be interpreted as limiting to the invention In FIG. 7a, distal optical element 1000 includes optical fiber 1001 encased in cap 109. Optical fiber 1001 includes optical axis 1002 having core 1004 surrounded by cladding 1005 further surrounded by jacket 1009. Optical fiber 1001 includes negative axicon 1006 etched at the distal end, centered on optical axis 1002, and having an angular extent A. Angular extent A is less than about 66° for typical glass. The maximum value of A is determined as twice the complement of the critical angle $\alpha$ for the optical material in core 1004. The complement of the critical angle is (90°−$\alpha$). Jacket 1009 is removed for a distance 1007 approximately the same as the depth of negative axicon 1006. When light travels through optical fiber 1001 and out of the distal end, it will be emitted approximately perpendicular to the optical axis 1002 near lateral line 1003 in a uniform 360 degree pattern. When used as an optical collector, optical fiber 1001 will collect light through a 360 degree angle from directions near lateral line 1003.

Figures 7A, 7B:
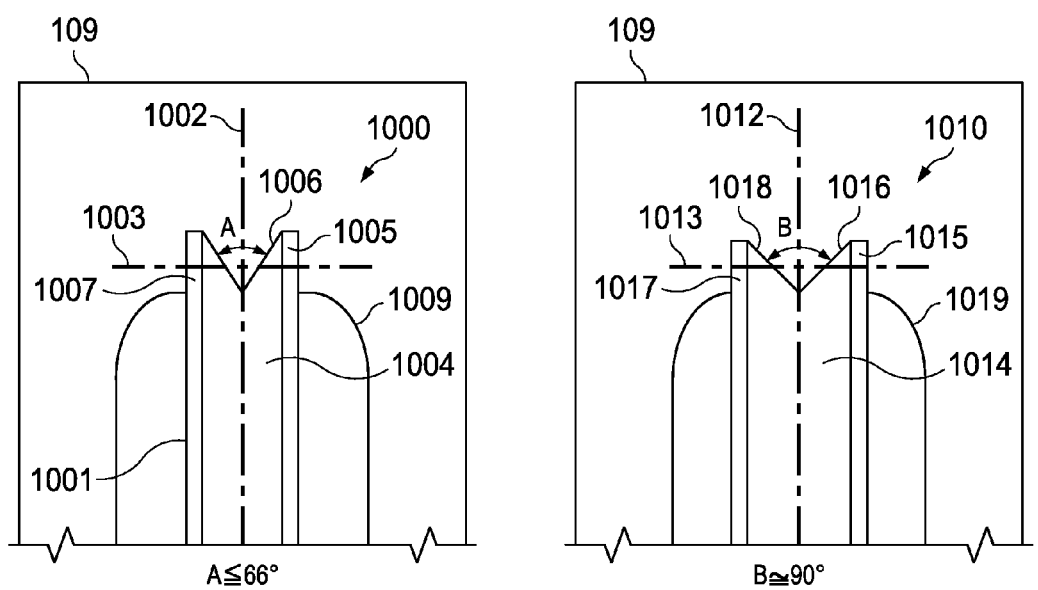
FIGS. 7a-7f show various embodiments of a distal optical element.

In FIG. 7b, distal optical element 1010 comprises an optical fiber 1011 covered by cap 109. Optical element 1010 includes optical axis 1012 having core 1014 surrounded by cladding 1015 which is further surrounded by jacket 1019. Optical fiber 1011 includes negative axicon 1016 etched at the distal end, centered on optical axis 1012, and having an angular extent B. Angular extent B is approximately 90°. Jacket 1019 is removed for a distance 1017 approximately the same as the depth of negative axicon 1016. Outer surface of negative axicon 1016 is coated with a reflective coating 1018. When light travels through optical fiber 1011 and out of the distal end, it will be emitted approximately perpendicular to the optical axis 1012 near lateral line 1013 in a uniform 360 degree pattern. When used as an optical collector, optical fiber 1011 will collect light from through a 360 degree angle from directions near the lateral line 1013.

A negative axicon can be fabricated in an optical fiber end by a chemical etching process using about a 50% solution of hydrofluoric acid with a buffer of $NH_4F$ in deionized water. Volume ratio of HF to buffer is varied to achieve varying negative axicon angles.

Figure 7C:
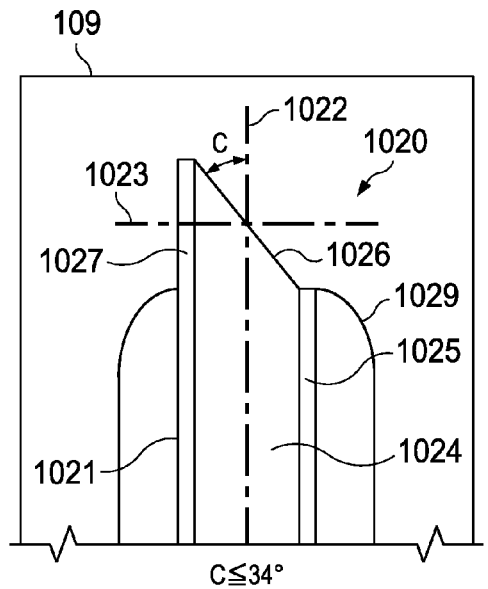

In FIG. 7c, distal optical element 1020 is enclosed in cap 109 and comprises optical fiber 1021. Optical fiber 1021 includes optical axis 1022 having core 1024 surrounded by cladding 1025 which is further surrounded by jacket 1029. Optical fiber 1021 includes beveled surface 1026 etched at the distal end at an angle C. Angle C is less than about 34° for typical glass. The value of C is determined as the complement of the critical angle for the optical material in core 1024. Jacket 1029 is removed for a distance 1027 approximately the same as the depth of beveled surface 1026. When light travels through optical fiber 1021 and out of the distal end, it will be emitted approximately perpendicular to the optical axis 1022 near lateral line 1023 in an angular pattern determined by the position of the beveled surface. When used as an optical collector, optical fiber 1021 will collect light in the approximate angular pattern from horizontal directions near the lateral line 1023.

Figure 7D:
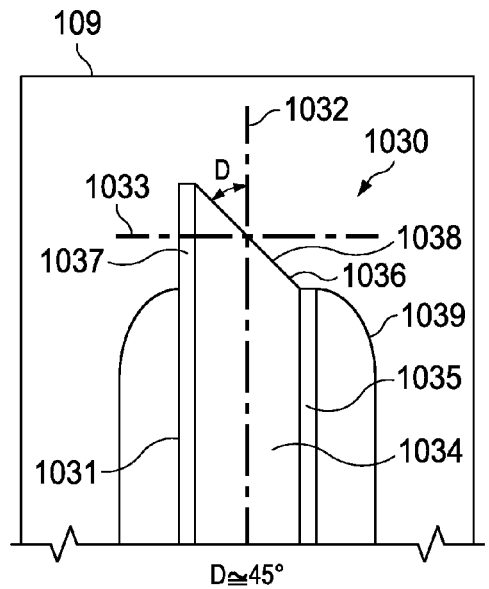

In FIG. 7d, distal optical element 1030 is encased in transparent cap 109 and comprises optical fiber 1031. Optical fiber 1031 includes optical axis 1032 having core 1034 surrounded by cladding 1035 which is further surrounded by jacket 1039. Optical fiber 1031 includes a beveled surface 1036 etched at the distal end at an angle D where D is about 45°. Beveled surface 1036 has a reflective coating 1038. Jacket 1039 is removed for a distance 1037 approximately the same as the depth of beveled surface 1036. When light travels through optical fiber 1031 and out of the distal end, it will be emitted approximately perpendicular to the optical axis 1032 near lateral line 1033 in an angular pattern determined by the position of the beveled surface. When used as an optical collector, optical fiber 1031 will collect light approximately in the angular pattern from horizontal directions near the lateral line 1033.

Figure 7E:
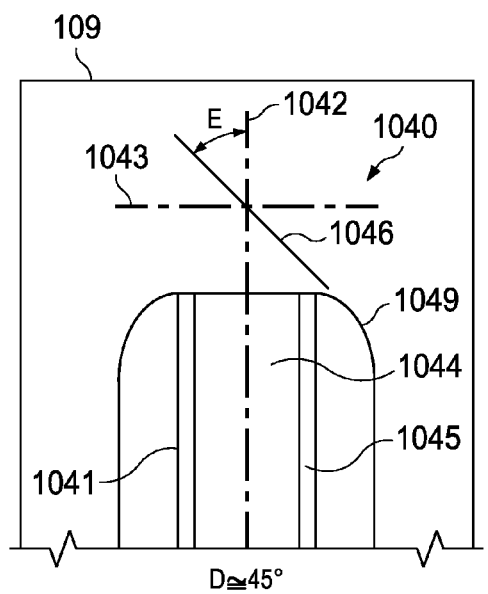

In FIG. 7e, distal optical element 1040 is encased by transparent cap 109. Distal optical element 1040 includes optical fiber 1041 with optical axis 1042 having core 1044. Core 1044 is surrounded by cladding 1045 which is further surrounded by jacket 1049. Reflecting surface 1046 is positioned above the distal end of the optical fiber at an angle E where E is about 45°. When light travels through optical fiber 1041 and out of the distal end, it will be emitted approximately along the optical axis 1042, reflected from reflecting surface 1046, and further emitted in a horizontal range of directions near lateral line 1043 in an approximate angular pattern determined by the aperture of the optical fiber, the aperture of the reflecting surface and the wavelength of the emitted light. When used as an optical collector, optical fiber 1041 will collect light in the approximate angular pattern from the horizontal range of direction near lateral line 1043.

Figure 7F:
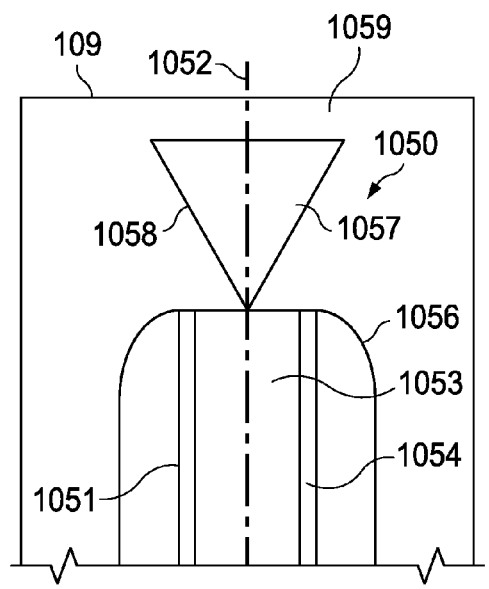

FIG. 7f, distal optical element 1050 is encased by transparent cap 109. Distal optical element 1050 includes optical fiber 1051 with optical axis 1052 and core 1053. Core 1053 is surrounded by cladding 1054 which is further surrounded by jacket 1056. Reflector 1057 is positioned adjacent optical fiber 1051 and coaxial with optical axis 1052. In a preferred embodiment, reflector 1057 is conical, that includes silvered surface 1058. In use, light transmitted from the optical fiber is reflected in a 360° pattern, generally perpendicular to optical axis 1052. Similarly, reflector 1057 collects light from a 360° axis and transmits it through optical fiber 1051, generally parallel to optical axis 1052. In a preferred embodiment, transparent cap 109 is filled with an optically transparent plastic matrix which supports and positions reflector 1057 above optical fiber 1051. In an alternative embodiment, reflector 1057 can be formed by a void in matrix 1059 which is internally silvered on surface 1058.

Referring to FIGS. 8a through 8d, a distal optical element configured as an optical emitter will be termed an optical emitter and a distal optical element configured as an optical collector will be termed an optical collector. The positional relationship between the optical emitters, the optical collectors and the stimulator electrodes during spinal movement will be described.

Figure 8A:
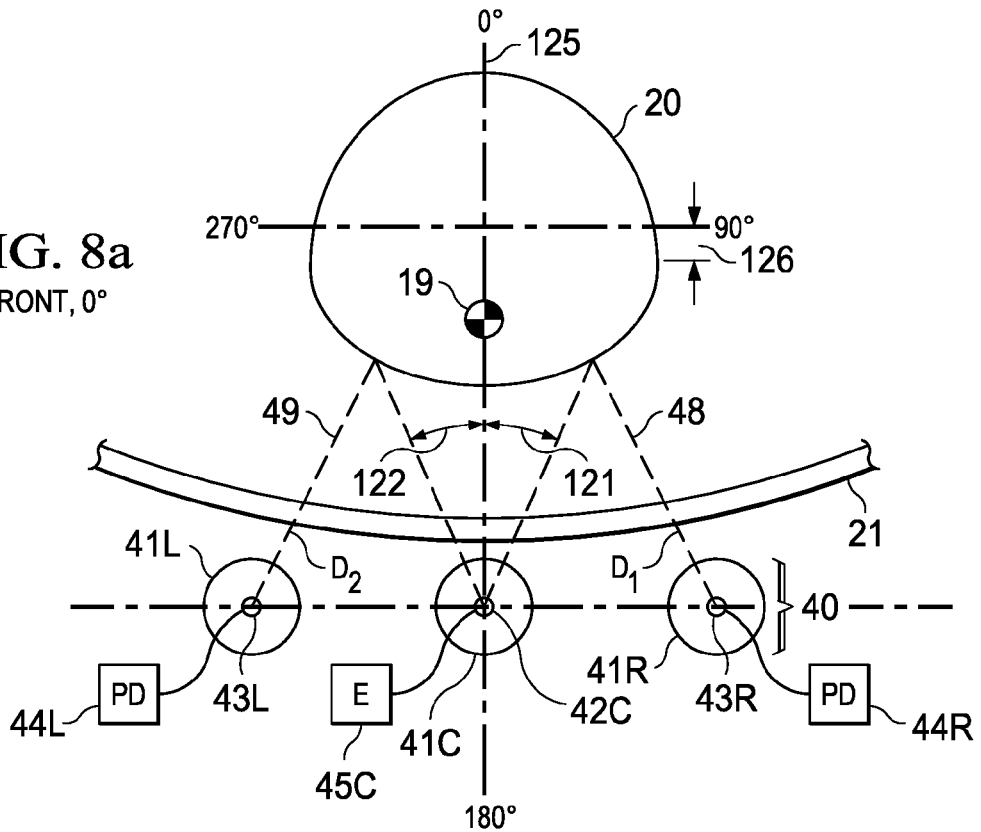
FIG. 8a shows a cross-sectional view of a first embodiment of a stimulator lead array centrally located in relation to a spinal cord at a forward position with 0° displacement.

Referring to FIG. 8a, spinal cord 20 is positioned forward towards a 0° direction in the spinal canal. Neurostimulator electrode assembly 40, implanted outside dura 21, includes central electrode 41C and optical emitter 42C on the distal end of a central stimulator lead; left electrode 41L and left optical collector 43L on the distal end of a left stimulator lead; and, right electrode 41R and right optical collector 43R on the distal end of a right stimulator lead. Optical emitter 42C is centrally positioned on optical axis 125 and emits light from IR emitter 45C coupled to the proximal end of the central stimulator lead. Electrodes 41L and 41R are positioned toward the dura and within an operational range of target cells 19. Left optical collector 43L is positioned within an operational range of spinal cord 20 and is coupled to photodetector 44L at the proximal end of the left stimulator lead. Right optical collector 43R is positioned within an operational range of the surface of spinal cord 20 and is coupled to photodetector 44R at the proximal end of the right stimulator lead. Target cells 19 are positioned within spinal cord 20 in an arbitrary but constant position with respect to the spinal cord.

In operation, optical emitter 42C produces light ray 48 which forms an angle 121 with optical axis 125. Light ray 48 is reflected from the surface of spinal cord 20, enters optical collector 43R, then collected by photodetector 44R and converted into a photocurrent $I_{R1}$ by photodetector 44R. Optical emitter 42C also produces light ray 49 which forms angle 122 with optical axis 125. Light ray 49 is reflected from the surface of spinal cord 20, enters optical collector 43L, then collected by photodetector 44L and converted into a photocurrent $I_{L1}$ at photodetector 44L. An electric field produced by electrode 41R stimulates target cells 19. Similarly, an electric field produced by electrode 41L stimulates target cells 19. Amplitudes $A_{L1}$ and $A_{R1}$ are the resulting currents to drive both the left and the right electrode, respectively. Light ray 48 traverses a distance $D_1$ between optical emitter 42C and right optical collector 43R. Light ray 49 traverses a distance of $D_2$ between optical emitter 42C and electrode 41L. The distances $D_1$ and $D_2$ are roughly equal and both relatively high. The photocurrents produced by the photodetectors 44R and 44L are roughly equal with a value of $I_{R1}$ and $I_{L1}$, respectively.

Figure 8B:
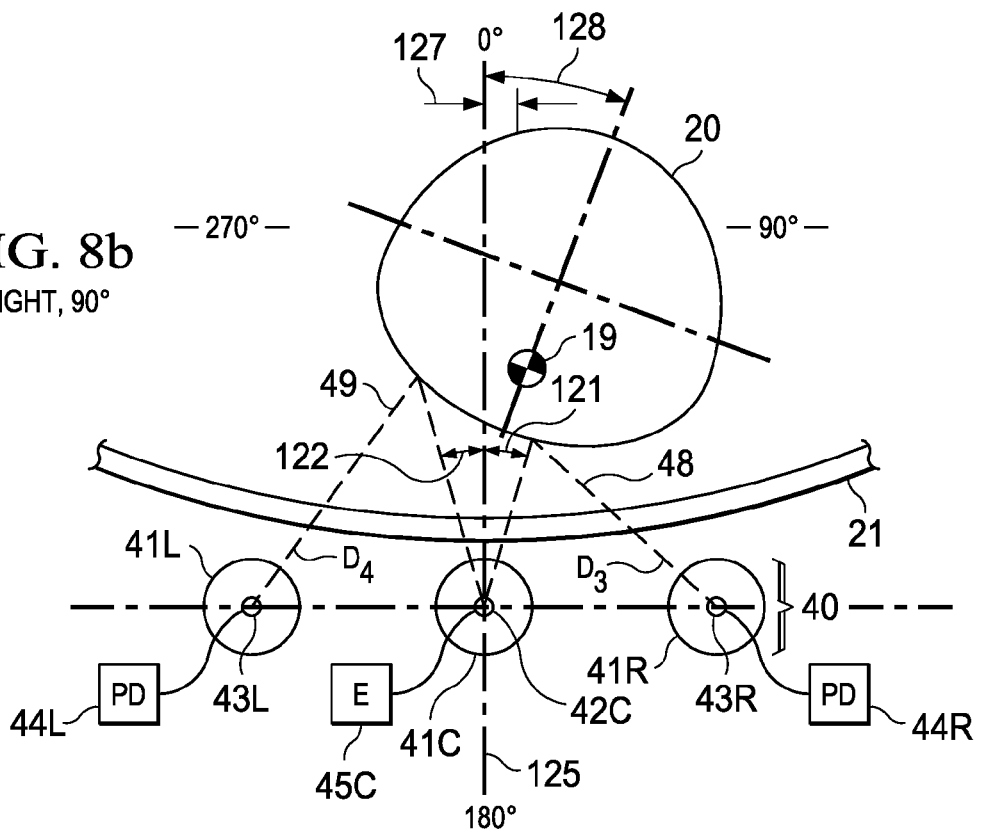
FIG. 8b shows a cross-sectional view of a first embodiment of a stimulator lead array located in relation to a spinal cord at a rightward position at 90° displacement.

Referring to FIG. 8b, the spinal cord is shifted to the right towards a 90° direction through linear translation 127 and rotated through angle 128 with respect to the forward position of FIG. 8a.

In operation, optical emitter 42C produces light ray 48 which forms an angle 121 with optical axis 125. Light ray 48 is reflected from the surface of spinal cord 20, enters right optical collector 43R, then collected by photodetector 44R which produces a photocurrent $I_{R2}$ in response. Optical emitter 42C also produces light ray 49 which forms an angle 122 with optical axis 125. Light ray 49 is reflected from the surface of spinal cord 20, enters left optical collector 43L, then collected by photodetector 44L which produces a photocurrent $I_{L2}$ in response. An electric field produced by electrode 41R stimulates target cells 19. Similarly, an electric field produced by electrode 41L stimulates target cells 19. The distance from electrode 41L to target cells 19 is greater than the distance from electrode 41R to target cells 19. Hence, to maintain a constant electric field at target cells 19, the current amplitude $A_{L2}$ for electrode 41L must be greater than the current amplitude $A_{R2}$ of the electrode 41R for the spinal cord position of FIG. 8b. The total distance traversed for light ray 48 is distance $D_3$. The total distance traversed by light ray 49 is distance $D_4$. It can be seen that distance $D_3$ is less than $D_1$ and $D_2$ and is relatively low. Distance $D_4$ is approximately equal to $D_1$ and $D_2$. The photocurrent $I_{L2}$ produced by photodetector 43L is much less than the photocurrent $I_{R2}$ produced by photodetector 43R.

Figure 8C:
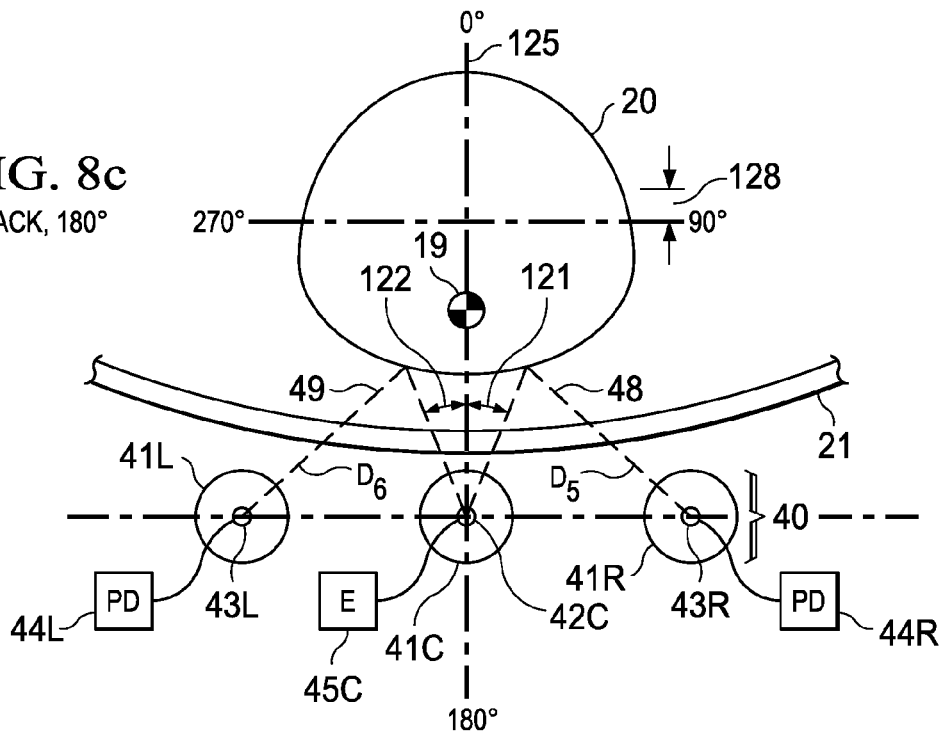
FIG. 8c shows a cross-sectional view of a first embodiment of a stimulator lead array centrally located in relation to a spinal cord at 180° displacement.
Figure 8D:
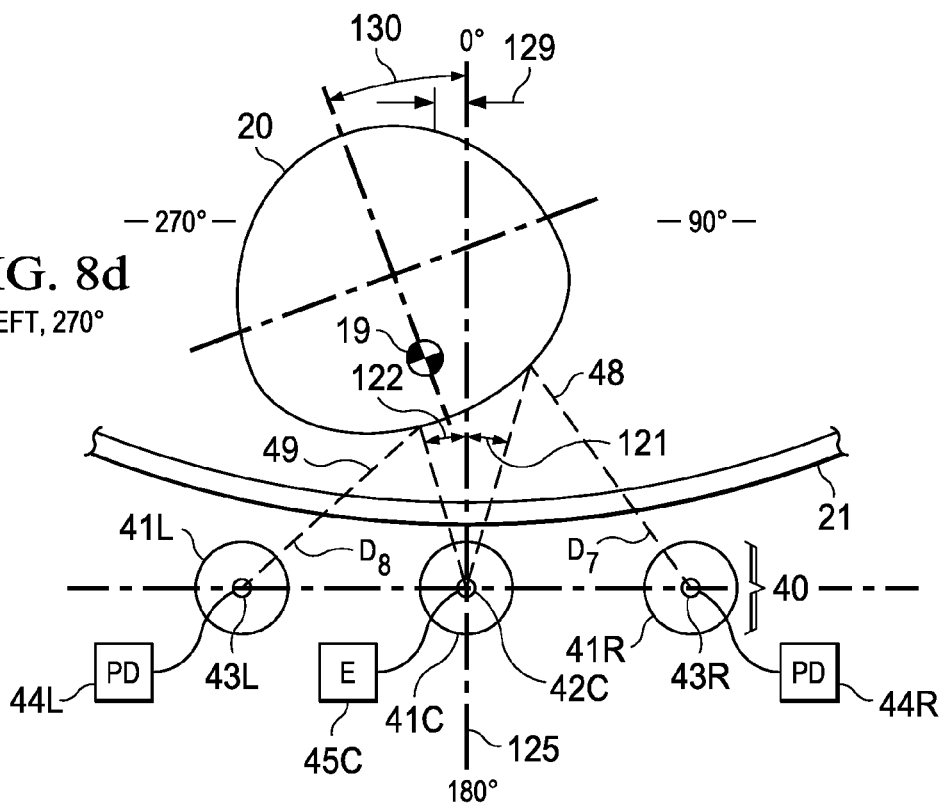
FIG. 8d shows a cross-sectional view of a first embodiment of a stimulator lead array located in relation to a spinal cord at 270° displacement.

Referring to FIG. 8c, spinal cord 20 is positioned rearward towards a 180° direction with linear translation 126 with respect to the forward position of FIG. 8a.

In operation, optical emitter 42C produces light ray 48 which forms an angle 121 with optical axis 125. Light ray 48 is reflected from surface of spinal cord 20, enters optical collector 43R, is then collected by photodetector 44R and converted into a photocurrent $I_{R3}$ in response. Optical emitter 42C also produces light ray 49 which forms an angle 122 with optical axis 125. Light ray 49 is reflected from the surface of spinal cord 20, enters left optical collector 43L, is then collected by photodetector 44L and converted into a photocurrent $I_{L3}$ in response. An electric field produced by electrode 41R stimulates target cells 19. Similarly, an electric field produced by electrode 41L stimulates target cells 19. The distances from left electrode 41L and right electrode 41R to target cells 19 are both smaller than $D_1$ or $D_2$. Hence, the current amplitude $A_{R3}$ to right electrode 41R and the current amplitude $A_{L3}$ to left electrode 41L are about the same, but relatively low compared to amplitudes $A_{R1}, A_{R2}, A_{L1}$ and $A_{L2}$. Light ray 48 traverses the distance $D_5$ between optical emitter 42C and right optical collector 43R. Light ray 49 traverses a distance $D_6$ between optical emitter 42C and left optical collector 43L. It can be seen that distances $D_5$ and $D_6$ are approximately equal. Distances $D_5$ and $D_6$ are less than distances $D_1$ and $D_2$. The photocurrent $I_{R3}$ produced by photodetector 44R and photocurrent $I_{L3}$ produced by photodetector 44L are about the same but both relatively high compared to the photocurrents $I_{R1}, I_{R2}, I_{L1}$ and $I_{L2}$.

Referring to 8d, the spinal cord 20 is shifted leftward towards a 270° direction in position by linear translation 129 and rotated through angle 130 with respect to the forward position of FIG. 8a.

In operation, optical emitter 42C produces light ray 49 which forms an angle 122 with optical axis 125. Optical emitter 42C also produces light ray 48 which forms angle 121 with optical axis 125. Light ray 49 is reflected from the surface of spinal cord 20, enters left optical collector 43L, is collected at photodetector 44L and converted to a photocurrent $I_{L4}$ in response. Light ray 48 is reflected from spinal cord 20, enters right optical collector 43R, is collected by photodetector 44R and converted to a photocurrent $I_{R4}$ in response. An electric field produced by electrode 41R stimulates target cells 19. Similarly, an electric field produced by electrode 41L stimulates target cells 19. The distance $D_8$ from left electrode 41L to the surface of spinal cord 20 is relatively low compared to the distance $D_7$ from the right electrode 41R to the surface of spinal cord 20. Hence, the current amplitude $A_{L4}$ for electrode 41L is relatively low compared to the current amplitude $A_{R4}$ for right electrode 41R. The distance traversed for light ray 49 is $D_8$. The distance traversed for light ray 48 is $D_7$. It can be seen that distance $D_7$ is greater than distance $D_8$. It can also be seen that distance $D_7$ is approximately equal to distances $D_1$ and $D_2$. It can further be seen that distance $D_8$ is approximately equal to distances $D_6$ and $D_5$. The photocurrent $I_{L4}$ produced by photodetector 44L is relatively high compared to the photocurrent $I_{R4}$ produced by photodetector 44R.

The relative relationship between received photodetector currents, $I_L$ and $I_R$, (from photodetectors 44L and 44R, respectively) and required current amplitudes of the current signals to the electrodes, $A_L$ and $A_R$, can be summarized in the following table for the four extreme positions of the spinal cord in the spinal canal.

TABLE 1

| Position | $I_L$ | $I_R$ | $A_L$ | $A_R$ |
|---|---|---|---|---|
| 1. Front - 0° | L | L | H | H |
| 2. Right - 90° | L | H | H | L |
| 3. Back - 180° | H | H | L | L |
| 4. Left - 270° | H | L | L | H |

Optical ratios associated with each photodetector pair correlate to a function of spinal cord position as determined ratiometrically (for side-to-side movement) and proportionally (for front-to-back movement) to the detected light intensities.

The ratio of the photocurrent signals from photodetector 44L and photodetector 44R is representative of spinal position left to right, $$r = I_L/I_R \quad (3)$$

In some embodiments, the ratio r is used to determine the proportional difference between left and right electrode current signals.

The difference between the photocurrent signals from photodetector 44L and photodetector 44R is also representative of spinal position left to right. In an alternate embodiment, the difference $$i_{diff} = I_R - I_L \quad (4)$$

is used to determine the proportional difference between left and right electrode current signals.

The total intensity of the photocurrent signals is representative of spinal position front to back. The total intensity can be represented by:

$$I_{total} = I_R + I_L \quad (5)$$

In an alternate embodiment, the total intensity is used to set the magnitude of both the left and right electrode current signals.

Referring to FIG. 9a, an alternate embodiment of a stimulator lead is shown. Stimulator lead 600 includes optical fiber 601 coupled to optical element 602 at a distal end and coupled to optical fiber connector 603 at a proximal end. Optical fiber connector 603 is further coupled to optical circulator 605. Optical circulator 605 is connected to first optical fiber 607, coupled to optical emitter 610, and second optical fiber 608, coupled to optical detector 611. Optical element 602 is configured as both an optical emitter and an optical collector.

A suitable optical circulator is the PIOC310P component from AC Photonics, Inc., of Santa Clara, Calif., operating at a wavelength of 1060 nm. Optical circulators of smaller size and operating at wavelengths longer than 1060 nm are also suited for these embodiments. Optical circulators of larger size and operating at wavelengths shorter than 1060 nm are also suited for these embodiments.

In use, a probe light beam 618 emitted from optical emitter 610 propagates through first optical fiber 607, through optical fiber 601, and exits from optical element 602. A responsive light beam 620 is collected by optical element 602 and propagates through optical fiber 601, through second optical fiber 608 and detected by optical detector 611. Optical circulator 605 allows responsive light beam 620 to propagate into second optical fiber 608 but not into first optical fiber 607. Optical circulator 605 also allows probe light beam 618 to propagate into optical fiber 601 but not into second optical fiber 608.

Responsive light beam 620 is generated through interaction between probe light beam 618 and tissue within the spinal cord. For example, probe light beam propagates through spinal canal, experiences absorption, is reflected by components within the spinal canal, and then experiences additional absorption before being collected as a responsive light beam with a different intensity and a different spectral profile.

Referring to FIG. 9b, a cross-section of stimulator lead 600 is shown. Stimulator lead 600 includes sheathed outer surface 613 which encapsulates a set of electrode leads 617, lumen 615 and lumen 616 in filler material 612. Lumen 616 encloses optical fiber 601. Lumen 615 provides a hollow cavity for a wire stylet to be inserted into the lead cable for the purpose of directing the position of the lead cable while being inserted into the epidural space of a patient. In a preferred embodiment lumen 616 is centrally located in the electrode lead while lumen 615 is positioned off axis. In alternate embodiments, lumen 615 is centrally located. In a preferred embodiment, sheathed outer surface 613 includes an EMI shield. Filler material 612 preferably includes a polyimide polymer. Filler material 612 can also include additional materials with physical properties that enhance the EMI shielding capability.

Referring to FIG. 9c, placement of a set of stimulator leads is shown. The stimulator leads are positioned in the epidural space between the dura and the walls of the spinal canal. In a preferred embodiment, a pair of optical emitter/collectors 631 and 633 is situated side by side.

Multiple stimulator leads such as stimulator lead 600 can be assembled into a stimulator lead assembly. Referring to FIGS. 10a-10d, spinal cord 20 is shown in various respective positions in the spinal canal: forward towards the 0° direction, rightward toward the 90° direction and back, backward toward the 180° direction, and leftward toward the 270° direction and back. Neurostimulator electrode assembly 40 is implanted outside dura 21 having a left stimulator lead with left electrode 244 and left distal optical element 245 and having a right stimulator lead with right electrode 242 and right distal optical element 243. Left distal optical element 245 is optically coupled to IR emitter $E_L$ and photodetector $PD_L$. Right distal optical element is optically coupled to IR emitter $E_R$ and photodetector $PD_R$.

Electrodes 242 and 244 are positioned toward the dura and within an operational range of target cells 19. Target cells 19 are positioned within spinal cord 20 in an arbitrary but constant position with respect to the spinal cord.

It should be understood that photodetector $PD_L$ will receive light originating from both IR emitters $E_L$ and $E_R$, and that photodetector $PD_R$ will receive light originating from both IR emitters $E_L$ and $E_R$. Various techniques can be used to separate the photocurrents derived from the two IR emitters. For example, IR emitter $E_L$ and IR emitter $E_R$ are alternatively powered on and the left and right photocurrents are temporally separated. The photocurrents detected while IR emitter $E_L$ is powered on are $I_{LL}$ at $PD_L$ and $I_{LR}$ at $PD_R$. The photocurrents detected while IR emitter $E_R$ is powered on are $I_{RR}$ at $PD_R$ and $I_{RL}$ at $PD_L$.

Figure 10A:
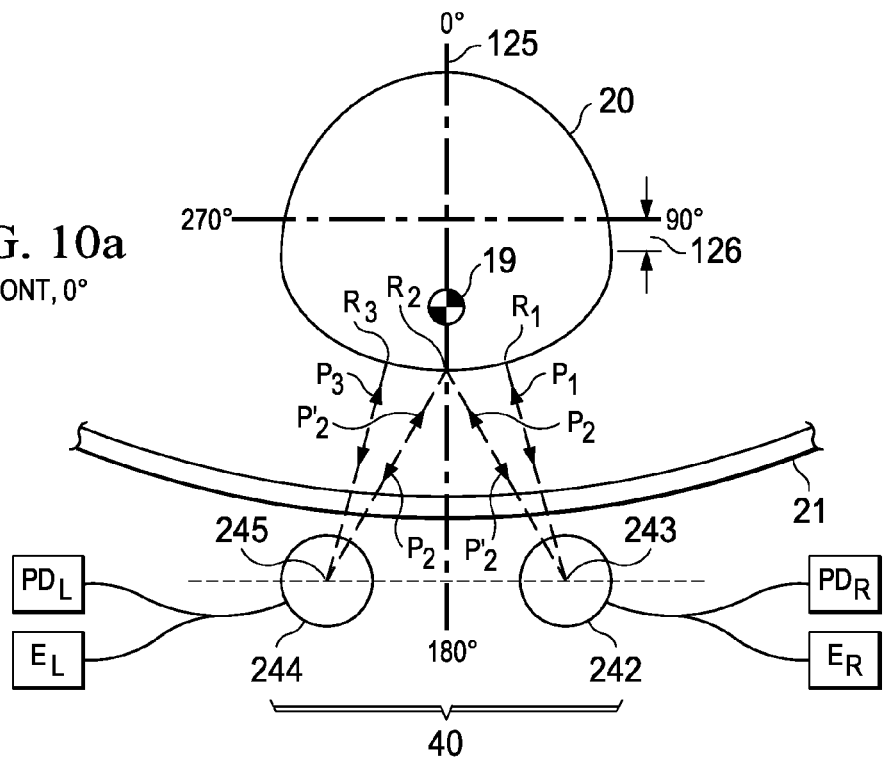
FIG. 10a shows a cross-sectional view of a second embodiment of a stimulator lead array centrally located in relation to a spinal cord at a forward position with 0° displacement.

Referring to FIG. 10a, wherein the spinal cord is positioned forward, path $P_1$ defines a light path from right distal optical element 243 to reflection point $R_1$ and back to right distal optical element 243. Path $P_3$ defines a light path from left distal optical element 245 to reflection point $R_3$ and back to left distal optical element 245. Path $P_2$ defines a light path from right distal optical element 243 to reflection point $R_2$ and then to left distal optical element 245. Path $P_{2'}$ defines a light path from left distal optical element 245 to reflection point $R_2$ and then to right distal optical element 243. The length of path $P_1$ is $D_1$; the length of path $P_3$ is $D_3$; and, the lengths of paths $P_2$ and $P_{2'}$ is $D_2$. Right distal optical element 243 emits light along paths $P_1$ and $P_2$ from right IR emitter $E_R$ and left distal optical element 245 emits light $P_{2'}$ and $P_3$ from IR emitter $E_L$.

Left distal optical element 245 collects light from path $P_2$ after reflection at point $R_2$ from spinal cord 20 and after attenuation and scattering by intermediate epidural tissue. Left distal optical element 245 further collects light from path $P_3$ after reflection from spinal cord 20 at point $R_3$ and after attenuation and scattering by epidural tissue. Light collected by distal optical element 245, is detected by photodetector $PD_L$.

Right distal optical element 243 collects light from path $P_{2'}$ after reflection from spinal cord 20 at point $R_2$ and after attenuation and scattering by intermediate epidural tissue. Right distal optical element 243 further collects light from path $P_1$ after reflection at point $R_1$ from spinal cord 20 and after attenuation and scattering by epidural tissue. Light collected by right distal optical element 243 is detected by photodetector $PD_R$.

The distances $D_1$, $D_2$ and $D_3$ are roughly equal when the spinal cord is positioned as shown in FIG. 10a. The photocurrents produced by the photodetectors $PD_R$ and $PD_L$ due to light emitted from right distal optical element 243 are roughly equal with a value of $I_{RR1}$ and $I_{RL1}$, respectively. The photocurrents produced by the photodetectors $PD_L$ and $PD_R$ due to light emitted from left distal optical element 244 are roughly equal with a value of $I_{LL1}$ and $I_{LR1}$, respectively.

An electric field produced by right electrode 242 stimulates target cells 19. Similarly, an electric field produced by left electrode 244 stimulates target cells 19. Current amplitudes $A_{R1}$ and $A_{L1}$ are for the average currents supplied by right electrode 242 and left electrode 244, respectively having pulse widths $PW_1$ and pulse frequencies $PF_1$. For the position of the spinal cord in FIG. 10a, given a fixed pulse width $PW_1$ and a fixed pulse frequency $PF_1$, the current amplitudes $A_{R1}$ and $A_{L1}$ are approximately the same. These foregoing results are tabulated in Table 2, row 1.

Figure 10B:
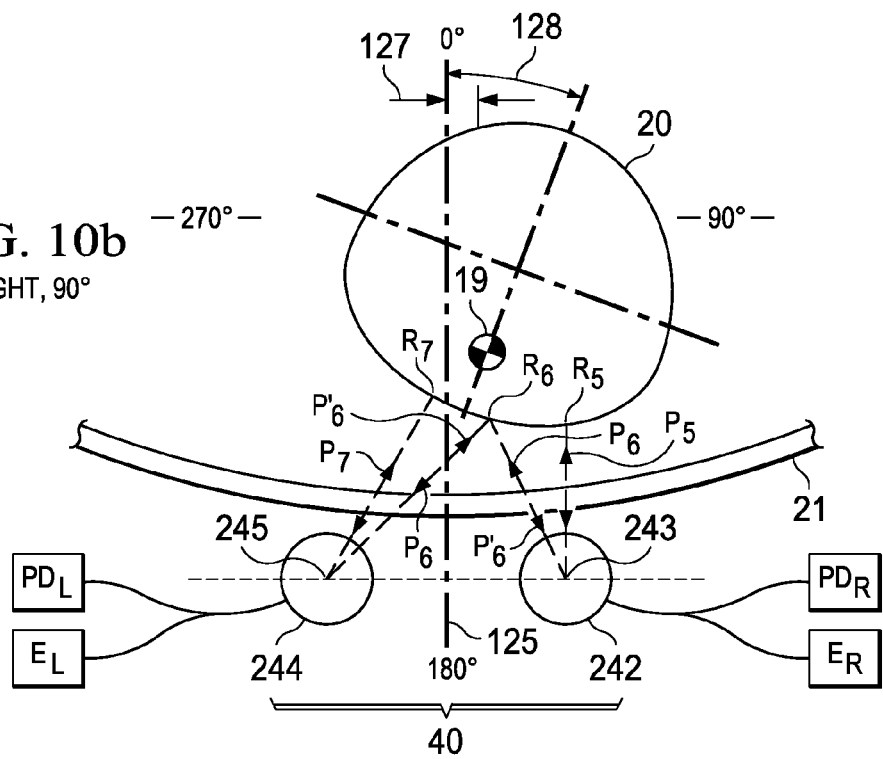
FIG. 10b shows a cross-sectional view of a second embodiment of a stimulator lead array located in relation to a spinal cord at a rightward position at 90° displacement.

Referring to FIG. 10b, wherein the spinal cord is positioned rightward and back, path $P_5$ defines a light path from right distal optical element 243 to reflection point $R_5$ and back to right distal optical element 243. Path $P_7$ defines a light path from left distal optical element 245 to reflection point $R_7$ and back to left distal optical element 245. Path $P_6$ defines a light path from right distal optical element 243 to reflection point $R_6$ and then to left distal optical element 245. Path $P_{6'}$ defines a light path from left distal optical element 245 to reflection point $R_6$ and then to right distal optical element 243. The length of path $P_5$ is $D_5$; the length of path $P_7$ is $D_7$; and, the lengths of paths $P_6$ and $P_{6'}$ is $D_6$. Right distal optical element 243 emits light along paths $P_5$ and $P_6$ from right IR emitter $E_R$ and left distal optical element 245 emits light $P_{6'}$ and $P_7$ from IR emitter $E_L$.

Left distal optical element 245 collects light from path $P_6$ after reflection at point $R_6$ from spinal cord 20 and after attenuation and scattering by intermediate epidural tissue. Left distal optical element 245 further collects light from path $P_7$ after reflection from spinal cord 20 at point $R_7$ and after attenuation and scattering by epidural tissue. Light collected by distal optical element 245, is detected by photodetector $PD_L$.

Right distal optical element 243 collects light from path $P_{6'}$ after reflection from spinal cord 20 at point $R_6$ and after attenuation and scattering by intermediate epidural tissue. Right distal optical element 243 further collects light from path $P_5$ after reflection at point $R_5$ from spinal cord 20 and after attenuation and scattering by epidural tissue. Light collected by right distal optical element 243 is detected by photodetector $PD_R$.

The distance $D_5$ is smaller than the distance $D_7$ and considerably smaller than the distance $D_6$: $D_5 < D_7 < D_6$. The photocurrents produced by the photodetectors $PD_R$ and $PD_L$ due to light emitted from right distal optical element 243 have values $I_{RR2}$ and $I_{RL2}$, respectively, where $I_{RR2} >> I_{RL2}$. The photocurrents produced by the photodetectors $PD_L$ and $PD_R$ due to light emitted from left distal optical element 245 have values $I_{LL2}$ and $I_{LR2}$, respectively, where $I_{LL2} >> I_{LR2}$. Also, $I_{LR2}$ is approximately the same as $I_{RL2}$. Comparing photocurrents of the spinal cord positions of FIGS. 10a and 10b, $I_{LL2} > I_{LL1}$, $I_{LR2} > I_{LR1}$, $I_{RL2} > I_{RL1}$ and $I_{RR2} >> I_{RR1}$.

An electric field produced by right electrode 242 stimulates target cells 19. Similarly, an electric field produced by left electrode 244 stimulates target cells 19. Current amplitudes $A_{R2}$ and $A_{L2}$ are the average currents supplied delivered by right electrode 242 and left electrode 244, respectively having pulse widths $PW_2$ and pulse frequencies $PF_2$. For the position of the spinal cord in FIG. 10b, given a fixed pulse width $PW_2$ and a fixed pulse frequency $PF_2$, the current amplitude $A_{R2}$ is less than current amplitude $A_{L2}$. Comparing the electrode current amplitudes of FIGS. 10a and 10b: $A_{L2} \approx A_{L1}$ and $A_{R2} < A_{R1}$. The foregoing results are tabulated in Table 2, row 2.

Figure 10C:
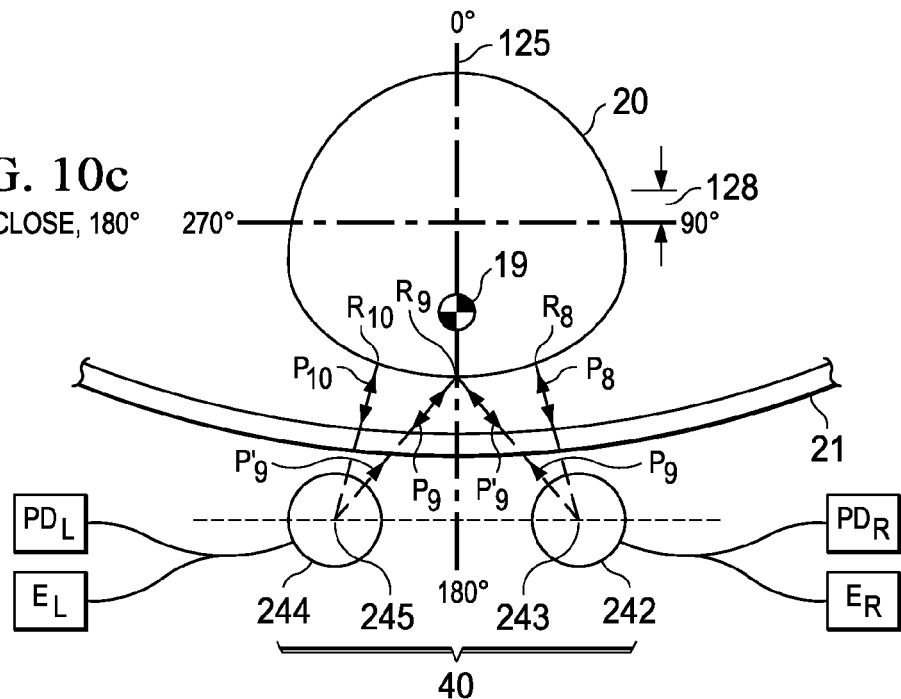
FIG. 10c shows a cross-sectional view of a second embodiment of a stimulator lead array centrally located in relation to a spinal cord at 180° displacement.

Referring to FIG. 10c, wherein the spinal cord is positioned towards the back. Path $P_8$ defines a light path from right distal optical element 243 to reflection point $R_8$ and back to right distal optical element 243. Path $P_{10}$ defines a light path from left distal optical element 245 to reflection point $R_{10}$ and back to left distal optical element 245. Path $P_9$ defines a light path from right distal optical element 243 to reflection point $R_9$ and then to left distal optical element 245. Path $P_{9'}$ defines a light path from left distal optical element 245 to reflection point $R_9$ and then to right distal optical element 243. The length of path $P_8$ is $D_8$; the length of path $P_{10}$ is $D_{10}$; and, the lengths of paths $P_9$ and $P_{9'}$ is $D_9$. Right distal optical element 243 emits light along paths $P_8$ and $P_9$ from right IR emitter $E_R$ and left distal optical element 245 emits light $P_{9'}$ and $P_{10}$ from IR emitter $E_L$.

Left distal optical element 245 collects light from path $P_9$ after reflection at point $R_9$ from spinal cord 20 and after attenuation and scattering by intermediate epidural tissue. Left distal optical element 245 further collects light from path $P_{10}$ after reflection from spinal cord 20 at point $R_{10}$ and after attenuation and scattering by epidural tissue. Light collected by distal optical element 245, is detected by photodetector $PD_L$.

Right distal optical element 243 collects light from path $P_9$, after reflection from spinal cord 20 at point $R_9$ and after attenuation and scattering by intermediate epidural tissue. Right distal optical element 243 further collects light from path $P_8$ after reflection at point $R_8$ from spinal cord 20 and after attenuation and scattering by epidural tissue. Light collected by right distal optical element 243 is detected by photodetector $PD_R$.

The distances $D_8$, $D_9$ and $D_{10}$ are roughly equal when the spinal cord is positioned backward. The photocurrents produced by the photodetectors $PD_R$ and $PD_L$ due to light emitted from right distal optical element 243 are roughly equal with a value of $I_{RR3}$ and $I_{RL3}$, respectively. The photocurrents produced by the photodetectors $PD_L$ and $PD_R$ due to light emitted from left distal optical element 245 are roughly equal with a value of $I_{LL3}$ and $I_{LR3}$, respectively. Comparing photocurrents for the positions of FIGS. 10a and 10c: $I_{RR3}>I_{RR1}$, $I_{RL3}>I_{RL1}$, $I_{LL3}>I_{LL1}$ and $I_{LR3}>I_{LR1}$.

An electric field produced by right electrode 242 stimulates target cells 19. Similarly, an electric field produced by left electrode 244 stimulates target cells 19. Current amplitudes $A_{R3}$ and $A_{L3}$ are the average currents supplied delivered by right electrode 242 and left electrode 244, respectively having pulse widths $PW_1$ and pulse frequencies $PF_1$. For the position of the spinal cord in FIG. 10c, given a fixed pulse width $PW_1$ and a fixed pulse frequency $PF_1$, the current amplitudes $A_{R3}$ and $A_{L3}$ are approximately the same. Comparing the electrode currents for the positions of FIGS. 10a and 10c, $A_{R1}>A_{R3}$ and $A_{L1}>A_{L3}$. The foregoing results are tabulated in Table 2, row 3.

Figure 10D:
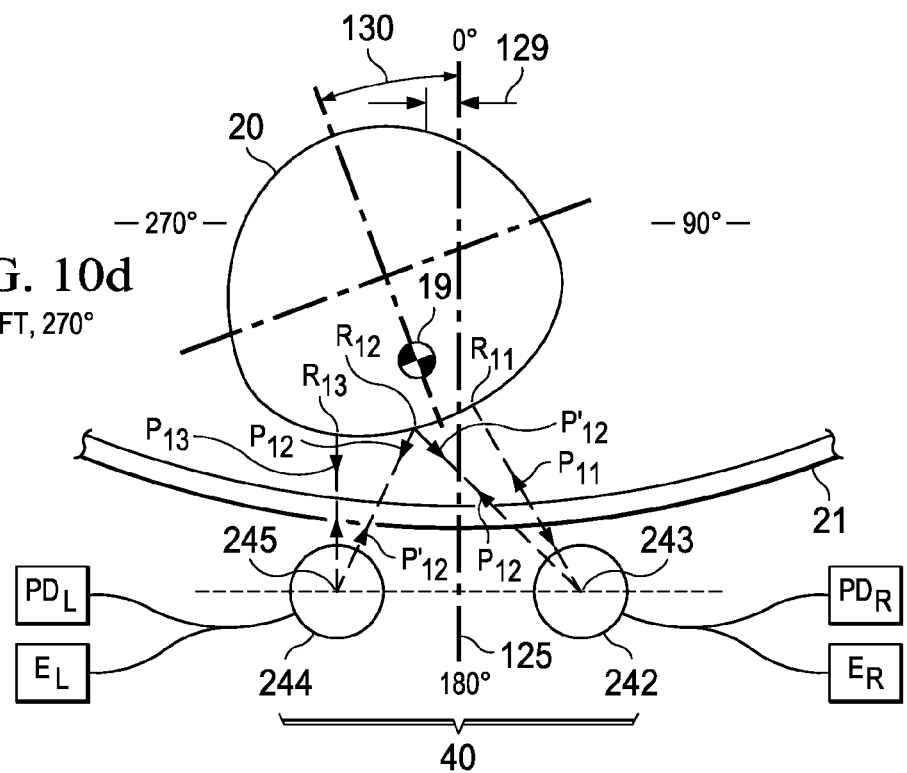
FIG. 10d shows a cross-sectional view of a second embodiment of a stimulator lead array located in relation to a spinal cord at 270° displacement

Referring to FIG. 10d, wherein the spinal cord is positioned leftward and back, path $P_{11}$ defines a light path from right distal optical element 243 to reflection point $R_{11}$ and back to right distal optical element 243. Path $P_{13}$ defines a light path from left distal optical element 245 to reflection point $R_{13}$ and back to left distal optical element 245. Path $P_{12}$ defines a light path from right distal optical element 243 to reflection point $R_{12}$ and then to left distal optical element 245. Path $P_{12'}$ defines a light path from left distal optical element 245 to reflection point $R_{12}$ and then to right distal optical element 243. The length of path $P_{11}$ is $D_{11}$; the length of path $P_{13}$ is $D_{13}$; and, the lengths of paths $P_{12}$ and $P_{12'}$ is $D_{12}$. Right distal optical element 243 emits light along paths $P_{11}$ and $P_{12}$ from right IR emitter $E_R$ and left distal optical element 245 emits light $P_{12'}$ and $P_{13}$ from IR emitter $E_L$.

Left distal optical element 245 collects light from path $P_{13}$ after reflection at point $R_{13}$ from spinal cord 20 and after attenuation and scattering by intermediate epidural tissue. Left distal optical element 245 further collects light from path $P_{12}$ after reflection from spinal cord 20 at point $R_{12}$ and after attenuation and scattering by epidural tissue. Light collected by distal optical element 245, is detected by photodetector $PD_L$.

Right distal optical element 243 collects light from path $P_{12'}$ after reflection from spinal cord 20 at point $R_{12}$ and after attenuation and scattering by intermediate epidural tissue. Right distal optical element 243 further collects light from path $P_{11}$ after reflection at point $R_{11}$ from spinal cord 20 and after attenuation and scattering by epidural tissue. Light collected by right distal optical element 243 is detected by photodetector $PD_R$.

The distance $D_{13}$ is smaller than the distance $D_{11}$ and considerably smaller than the distance $D_{12}$: $D_{13}<D_{11}<D_{12}$. The photocurrents produced by the photodetectors $PD_R$ and $PD_L$ due to light emitted from right distal optical element 243 have values $I_{RR4}$ and $I_{RL4}$, respectively where $I_{RR4}<<I_{RL4}$. The photocurrents produced by the photodetectors $PD_L$ and $PD_R$ due to light emitted from left distal optical element 245 have values $I_{LL4}$ and $I_{LR4}$, respectively, where $I_{RR4}<I_{LL4}<<I_{LR4}$. Also $I_{LR4}$ is approximately the same as $I_{RL4}$. Comparing photocurrents of positions of FIGS. 10a and 10d, $I_{LL4}>>I_{LL1}$, $I_{LR4}>I_{LR1}$, $I_{RL4}>I_{RL1}$ and $I_{RR4}>I_{RR1}$.

An electric field produced by right electrode 242 stimulates target cells 19. Similarly, an electric field produced by left electrode 244 stimulates target cells 19. Current amplitudes $A_{R4}$ and $A_{L4}$ are the average currents supplied delivered by right electrode 242 and left electrode 244, respectively having pulse widths $PW_4$ and pulse frequencies $PF_4$. For the position of the spinal cord in FIG. 10d, given a fixed pulse width $PW_4$ and a fixed pulse frequency $PF_4$, the current amplitude $A_{L4}$ is less than current amplitude $A_{R4}$. Comparing the electrode current amplitudes of FIGS. 10a and 10d: $A_{L4}<A_{L1}$ and $A_{R4}\approx A_{R1}$. The foregoing results are tabulated in Table 2, row 4.

The relative relationship between received photodetector currents and required current amplitudes of the current signals to the electrodes, $A_L$ and $A_R$, can be summarized in the following table for the four example positions of the spinal cord in the spinal canal.

TABLE 2

| Position | Emitter L Detector L | Emitter L Detector R | Emitter R Detector R | Emitter R Detector L | $A_L$ | $A_R$ |
|---|---|---|---|---|---|---|
| 1. Front 0° | L | L | L | L | H | H |
| 2. Back-right 90° | L | M | H | M | H | L |
| 3. Back-180° | H | H | H | H | L | L |
| 4. Back-left 270° | H | M | L | M | L | H |

Optical ratios associated with each photodetector correlate to a function of spinal cord position as determined ratiometrically (for side-to-side movement) and proportionally (for front-to-back movement) to the detected light intensities.

The ratio of the total photocurrent signals from photodetector $PD_L$ to the total current signals from photodetector $PD_R$ is representative of spinal position left to right.

$$r = \frac{(I_{LL} + I_{LR})}{(I_{RR} + I_{RL})} \tag{6}$$

In an alternate embodiment, the ratio r is used to determine the proportional difference between $A_L$ and $A_R$.

The difference between the total photocurrent signals from photodetector $PD_L$ to the total current signals from photodetector $PD_R$ is also representative of spinal position left to right.

$$I_{diff}=(I_{LL}+I_{LR})-(I_{RR}+I_{RL})\approx I_{LL}-I_{RR}$$

In an alternate embodiment, the photocurrent difference $I_{diff}$ is used to determine the proportional difference between $A_L$ and $A_R$.

The total photocurrent of all four photodetector current signals is representative of spinal position front to back, where the total photocurrent is:

$$I_{total}=I_{RR}+I_{RL}+I_{LL}+I_{LR} \tag{8}$$

In an alternate embodiment, the total photocurrent $I_{total}$ is used to determine the overall magnitude of $A_L$ and $A_R$.

Figures 11A, 11B:
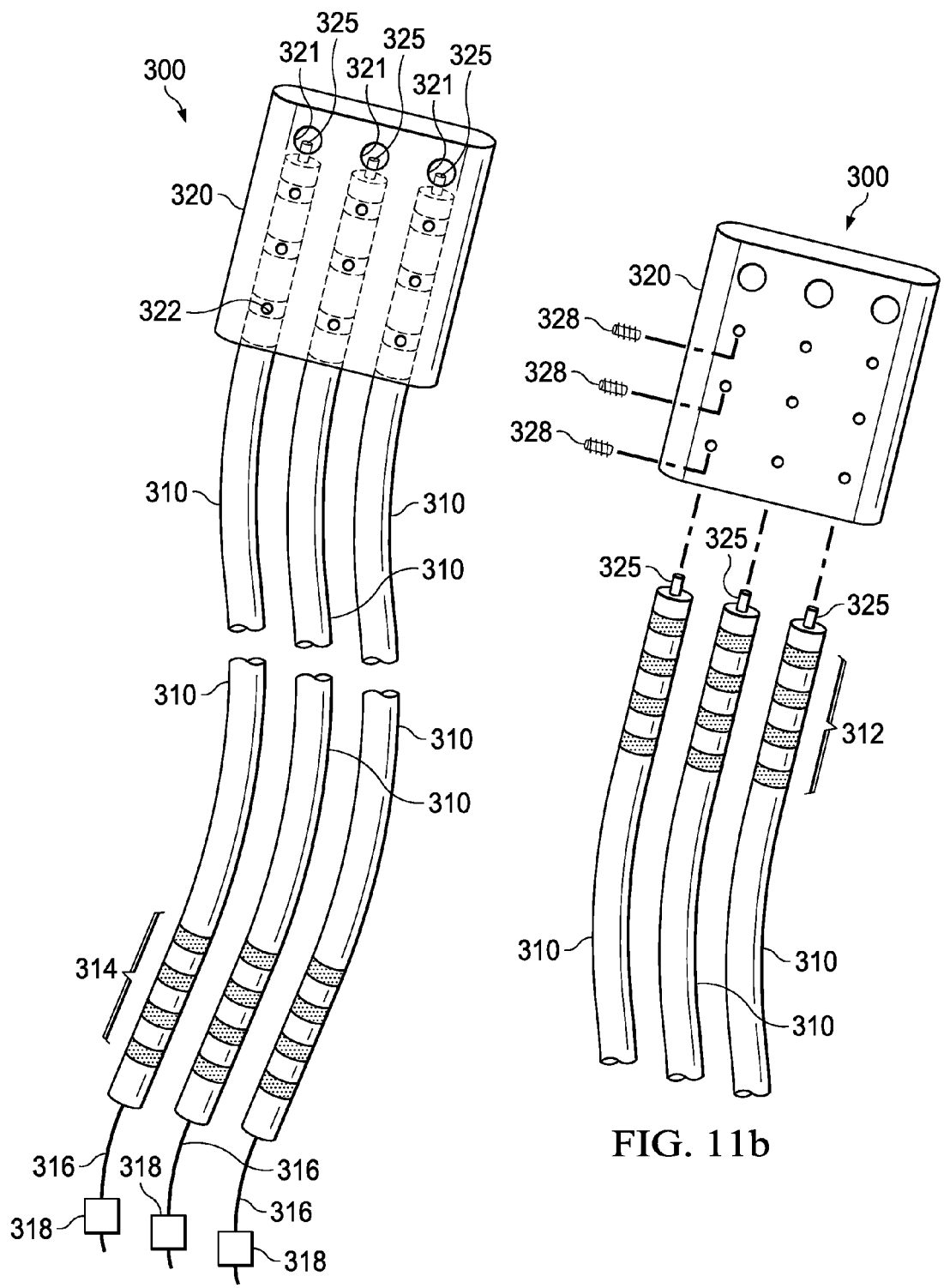
FIGS. 11a-11c show a distal end cap for multiple stimulator leads.

Referring to FIGS. 11a and 11b, an alternate embodiment of a stimulator lead assembly is shown. Stimulator lead assembly 300 includes a set of stimulator leads 310 having a distal end and a proximal end and incorporating a set of optical fibers 316. The set of stimulator leads 310 further incorporate a set of electrical wires which terminate on the proximal end in set of electrode contacts 314 and at the distal end in set of electrode contacts 312. The set of optical fibers 316 terminate on the proximal end in a set of fiber optic connectors 318 and at the distal end in a set of distal optical elements 325. Electrode housing 320 has a set of electrode contacts 322 contacting the set of electrode contacts 312. Electrode housing 320 further includes a set of cavities 321 containing the set of distal optical elements 325 and optically isolating the set of distal optical elements from each other. In the embodiment shown, set of electrode contacts 322 include a set of set screws 328 threaded into a set of threaded holes in electrode housing to electrically and mechanically attach the set of stimulator leads to the electrode housing.

Figure 11C:
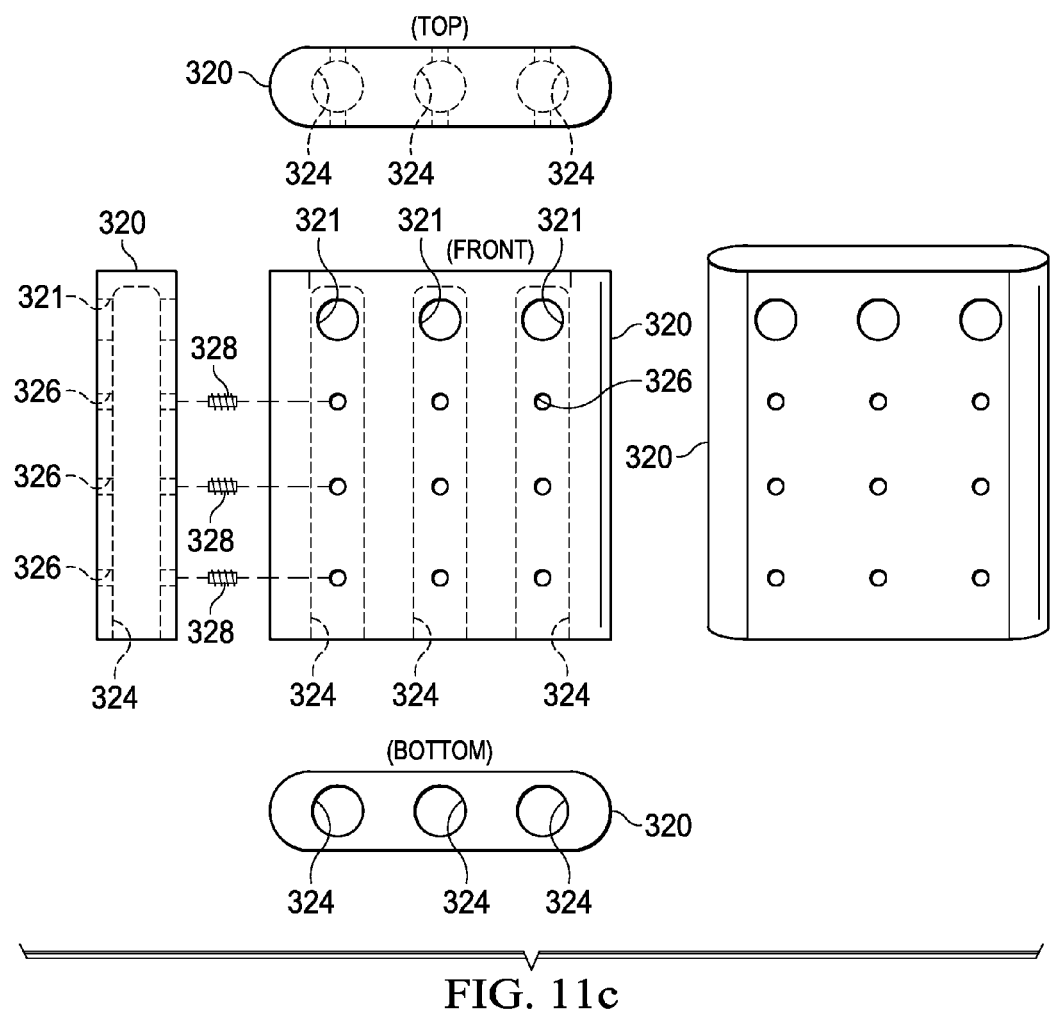

Referring to FIG. 11c, electrode housing 320 further comprises a set of holes 324 ductedly connected to set of cavities 321 and a set of threaded holes 326. Set of set screws 328 thread into set of threaded holes 326.

Figure 12:
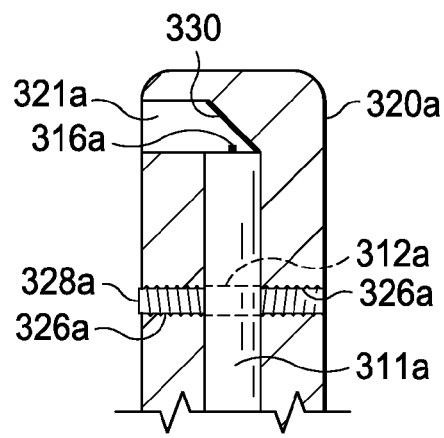
FIG. 12 shows a distal end cap configuration with a flat reflective surface.

FIG. 12 shows a side cross-section of electrode housing 320a. Cavity 321a of set of cavities 321 includes reflective surface 330 above the distal end of optical fiber 316a. Reflective surface 330 is polished approximately flat and at about a 45° angle to the optical axis of optical fiber 316a. Stimulator lead 311a is held in place by set screw 328a threaded into threaded hole 326a and fastened against stimulator electrode 312a.

Figure 13A:
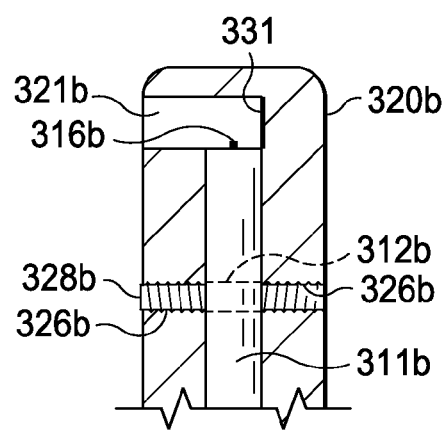
FIGS. 13a and 13b show a distal end cap with a curved reflective surface.
Figure 13B:
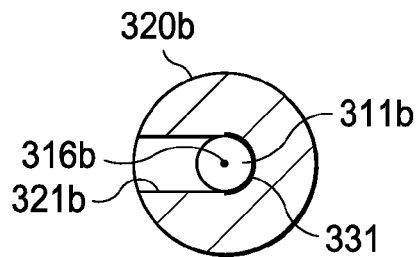

FIG. 13a shows a side view cross-section of electrode housing 320b. FIG. 13b shows a top view cross-section of electrode housing 320b. Cavity 321b of set of cavities 321 includes a cylindrical reflective surface 331 surrounding the distal end of optical fiber 316b. Optical fiber 316b includes a negative axicon at the distal end. Stimulator lead 311b including stimulator electrode 312b is held in place by set screw 328b threaded into threaded hole 326b and fastened against stimulator electrode 312b.

An alternate embodiment of electrode housing 320 is arranged as in FIGS. 13a and 13b, but does not include the cylindrical reflective surface 331. The alternate embodiment utilizes one of either an optical fiber having a negative axicon at the distal end or an optical fiber having a beveled surface.

Figure 14:
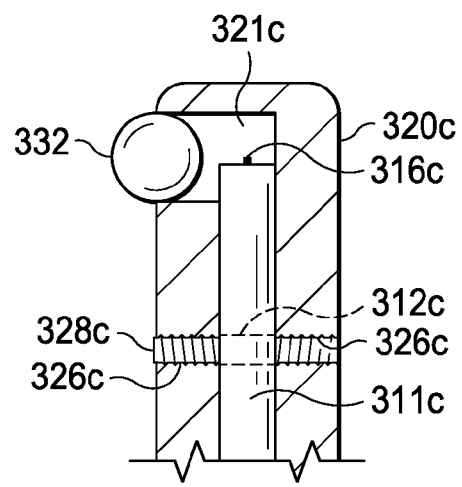
FIG. 14 shows a distal end cap incorporating a ball lens.

FIG. 14 shows a side cross-section of electrode housing 320c. Cavity 321c of set of cavities 321 includes ball lens 332 positioned at approximately a focal distance from the distal end of optical fiber 316c. Distal end of optical fiber 316c includes one of either a negative axicon or a beveled surface. Stimulator lead 311c including stimulator electrode 312c is held in place by set screw 328c threaded into threaded hole 326c and fastened against stimulator electrode 312c.

Figure 15:
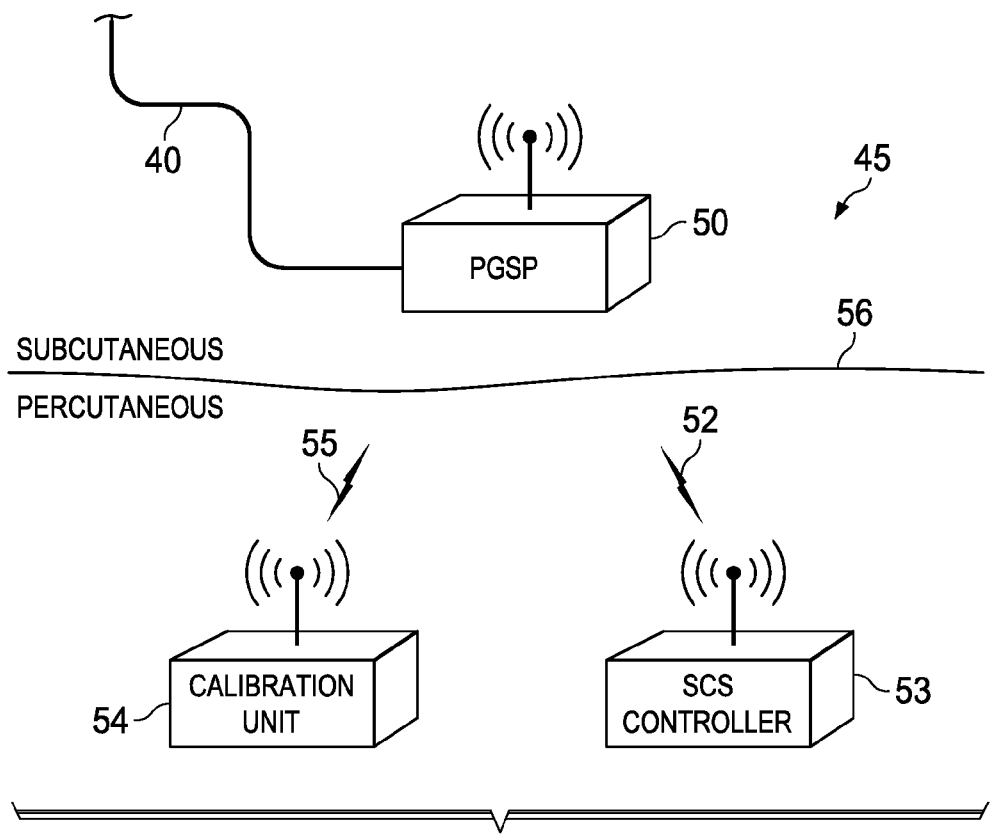
FIG. 15 shows a schematic representation of a preferred embodiment of the positionally sensitive spinal cord stimulation system.

Referring to FIG. 15, a preferred embodiment of the implanted components of the system is shown. Positionally-sensitive spinal cord stimulator 45 includes pulse generator and signal processor (PGSP) 50 and stimulator lead assembly 40. PGSP unit 50 provides power to a set of electrodes in stimulator lead assembly 40 and houses electronic and optoelectronic components of the system. Stimulator lead assembly 40 connects to PGSP unit 50 further connecting the stimulator electrodes of each stimulator lead to a controllable current source. Stimulator lead assembly 40 connects at least one IR emitter to at least one optical fiber through a first fiber optical connector and at least two photodetectors to at least two optical fibers through additional fiber optic connectors. PGSP unit 50 gathers and processes photodetector signals and makes adjustments to the stimulator electrode current (or voltage) based on the photodetector signals. PGSP unit 50 is connected by wireless communication link 52 across skin boundary 56 to SCS controller 53. The SCS controller is configured to allow percutaneous activation of and adjustments to positionally-sensitive spinal cord stimulator 45. PGSP unit 50 is also connected by wireless communication link 55 to calibration unit 54. Calibration unit 54 is programmed to accept patient feedback and transmit it to PGSP 50 during calibration. In an alternate embodiment, calibration unit 54 is incorporated into SCS controller 53.

PGSP unit 50 is preferably powered by batteries. In an alternate embodiment, PGSP unit 50 derives power from capacitive or inductive coupling devices. Calibration may further calibrate the batteries, the capacitive devices, or inductive coupling in PGSP unit 50. Communication links 52 or 55 may further serve as a means of providing electrical charge for the batteries or capacitive devices of PGSP unit 50.

Figure 16A:
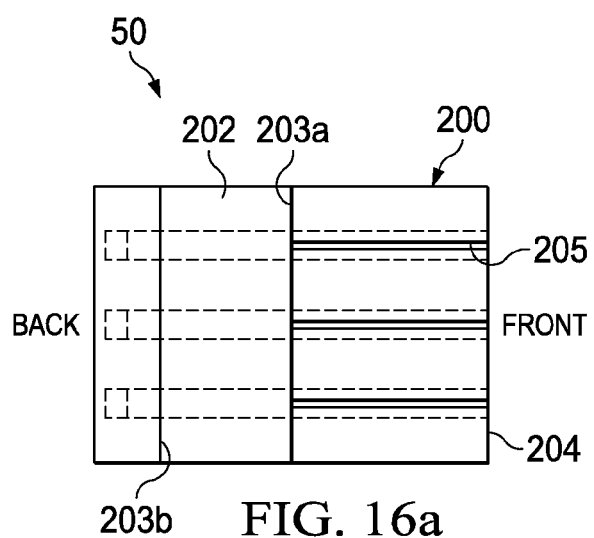
FIGS. 16a-16e show a physical drawing of a pulse generation and optical signal processing unit.
Figure 16B:
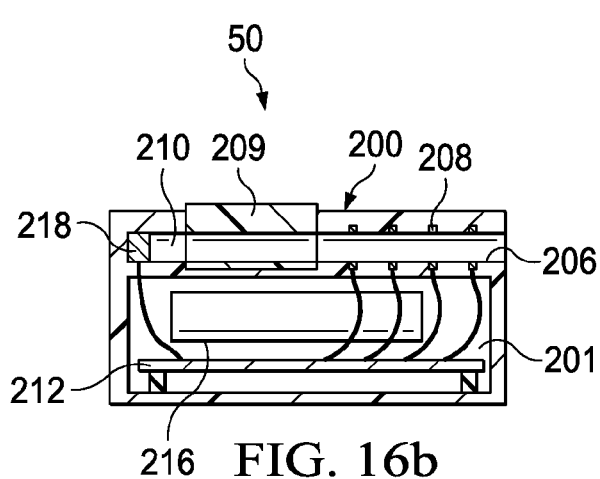
Figure 16C:
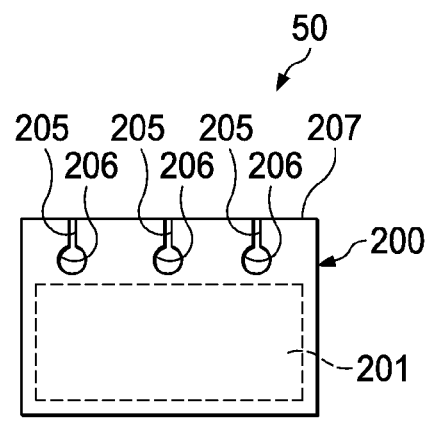

Referring to FIGS. 16a-16c, mechanical form of PGSP unit is shown. PGSP unit comprises housing 200 having top surface 207 and recess 202 with front wall 203a and back wall 203b. Cover 209 hermetically seals recess 202. Housing 200 further includes front face 204 and cavity 201 below recess 202 and below top surface 207. Cavity 201 contains and supports electronics board 212 and battery 216. A set of horizontal holes 206 extend through front face 204 into housing 200 and through front wall 203a. Each horizontal hole in the set of horizontal holes 206 includes a set of electrode contactors to match the set of proximal electrodes on the proximal end of a stimulator lead assembly. A set of slots 205 are cut from top surface 207 into the center of the set of horizontal holes 206. A set of fiber optical connectors 210 are mounted into housing 200 from back wall 203b and coupled to a set of active optical components 218. Each active optical component in set of active optical components 218 comprises at least one of the group consisting of an IR emitter and a photodetector. The set of fiber optic connectors 210 match the fiber optic connector on the proximal end of a stimulator lead assembly. Set of active optical components 218 are electrically coupled to and controlled by electronics board 212. Set of electrode contactors are electrically coupled to and driven by electronics board 212. Battery 216 powers electronics board 212.

Figure 16D:
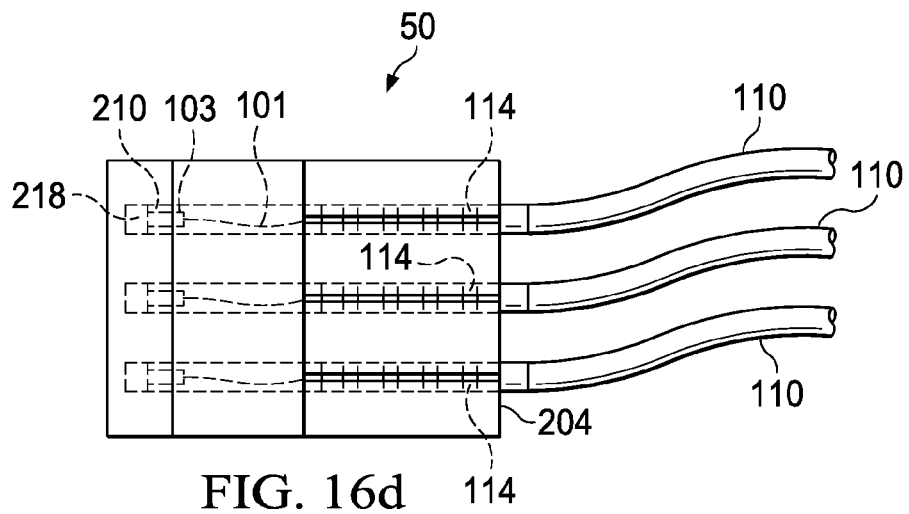
Figure 16E:
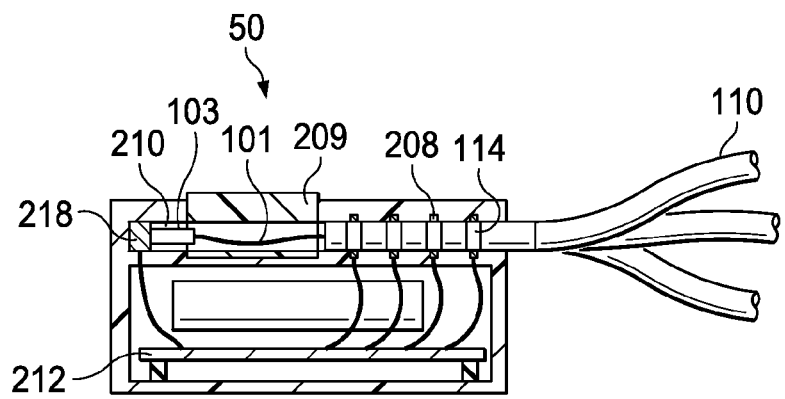

Referring to FIGS. 16d and 16e, PGSP unit 50 is shown with a set of stimulator lead assemblies inserted and mechanically engaged. Lead cable 110 is inserted into a horizontal hole in set of horizontal holes 206 causing proximal set of electrode contacts 114 to come into electrical contact with set of electrode contactors 208 and further connecting proximal set of electrode contacts to electronics board 212. Optical fiber 101 is brought through slot 205 and over recess 202 so that fiber optic connector 103 is inserted into set of fiber optic connectors 210 making a low loss optical connection between optical fiber 101 and active optical component 218. Lead cable 110 and optical fiber 101 are mechanically engaged into place.

Figure 17A:
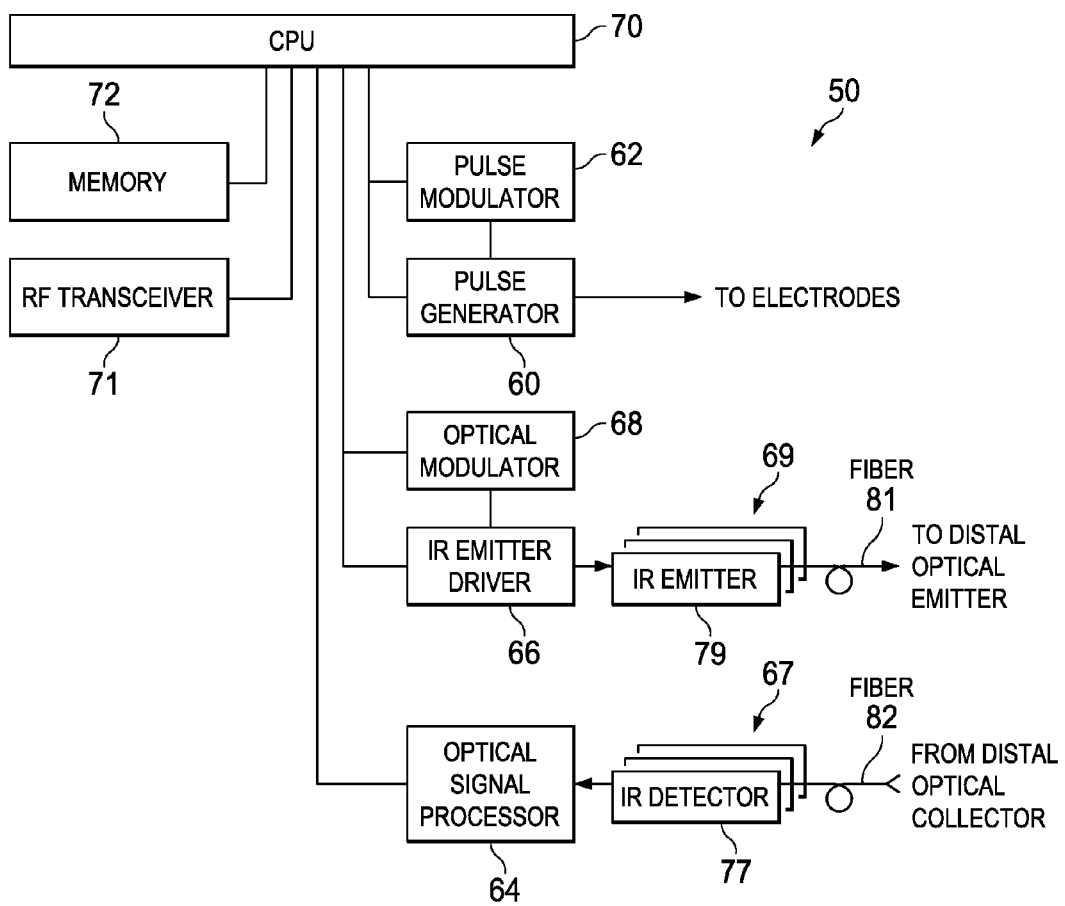
FIG. 17a is a block diagram of the components of a preferred embodiment of a pulse generation and optical signal processing unit.

Referring to FIG. 17a, block diagram of PGSP unit 50 is shown. PGSP unit 50 includes CPU 70 having onboard memory 72. CPU 70 is connected to pulse modulator 62 and pulse generator 60. Pulse modulator 62 is connected to pulse generator 60. CPU 70 is also operatively connected to optical modulator 68 and optical signal processor 64. Optical modulator 68 is connected to infrared emitter driver 66. Infrared emitter driver 66 is connected to IR emitter 79. IR emitter 79, in set of IR emitters 69 includes a fiber optic connector to effectively couple IR emitter 79 to fiber 81. Fiber 81 is connected to a distal optical emitter in the stimulator lead. Other IR emitters in set of IR emitters 69 are similarly connected to a set of optical fibers and a set of distal optical emitters.

CPU 70 is also connected to optical signal processor 64. Optical signal processor 64 is connected to a set of photodetectors 67 and receives signals from the set of photodetectors, filters the optical signals, and correlates the optical signals to an IR emitter amplitude, pulse width and frequency. Optical signal processor 64 may include a synchronized gated detection (e.g. lock-in amplifier type) function or other demodulation function to improve the signal to noise ratio of the detected light or to separate optical signals detected by one detector which was generated from multiple IR emitters.

IR detector 77, in set of photodetectors 67, is connected to optical signal processor 64. IR detector 77 translates incoming light pulses from fiber 82 into electrical signals processed by optical signal processor 64. IR detector 77 includes fiber optic connector to fiber 82 which is coupled to a distal optical collector. Other photodetectors in the set of photodetectors are similarly connected to a set of fibers and a set of optical collectors. In a preferred embodiment, the photodetectors are similar to that of Part No. APA3010P3Bt from Kingbright Corporation of City of Industry, Calif.

CPU 70 is connected to optical modulator 68. Optical modulator 68 generates the IR emission waveform transmitted to the set of IR emitters according to parameters set and transmitted by CPU 70. IR emitter driver 66 is connected to both optical modulator 68 and CPU 70. In operation, to send an IR light pulse, the CPU activates the optical modulator to generate an electrical waveform which is then transmitted to the IR emitter driver. The IR emitter driver transmits the waveform to IR emitter 79 and a pulse with the waveform is launched into fiber 81.

The optical waveform may take several forms. For example, the pulse width of the optical waveform may have a low duty cycle to minimize power consumption. A single optical pulse may occur for a set of electrode stimulation pulses. The optical waveform may include frequency, phase or amplitude modulation. Typical wavelength of the IR light from the set of IR emitters is 940 nm. Typical output intensity of the IR emitters is 1 to 2 mW and a suitable part is Part No. PDI-E900 from Advanced Photonix, Inc. of Ann Arbor, Mich.

Set of IR emitters 69 are driven by IR emitter driver 66. The IR emitter driver is programmably configured to drive the set of IR emitters such that in a first mode of operation, optical pulses are launched alternatively into multiple optical fibers. In a second mode of operation, a set of uniquely modulated optical waveforms are launched simultaneously in multiple optical fibers, each optical fiber carrying one uniquely modulated optical waveform. In a third mode of operation, optical pulses are launched simultaneously into multiple optical fibers, each optical pulse having the same waveform. The first, second and third modes of operation are operationally equivalent when there is only one IR emitter in the set of IR emitters.

Pulse generator 60 is connected to the set of electrodes in electrode assembly 40. In order to generate a pulse to the electrodes, the CPU consults a calibration table stored in onboard memory 72 to determine pulse width $P_W$, pulse frequency $P_f$ and pulse amplitudes $A_L$ and $A_R$ for the left and right electrodes, respectively. The pulse width and frequency are transmitted to pulse modulator 62 which creates a modified square wave signal. The modified square wave signal is passed to pulse generator 60. CPU 70 passes the amplitude for the left and right electrodes to pulse generator 60 in digital form. Pulse generator 60 then amplifies the modified square wave according to $A_L$ and $A_R$ to form left and right modified square wares and transmits them to the left and right electrodes, respectively.

The modified square wave has an amplitude and duration (or width). Pulse widths varying from 20 to 1000 microseconds have been shown to be effective. The frequency of the pulse waveforms between 20 and 1000 hertz have been shown to be effective. The output amplitude is preferably from 0 (zero) to +/−20 mA or 0 (zero) to +/−10 V but may vary beyond those ranges according to patient sensitivity.

Figure 17B:
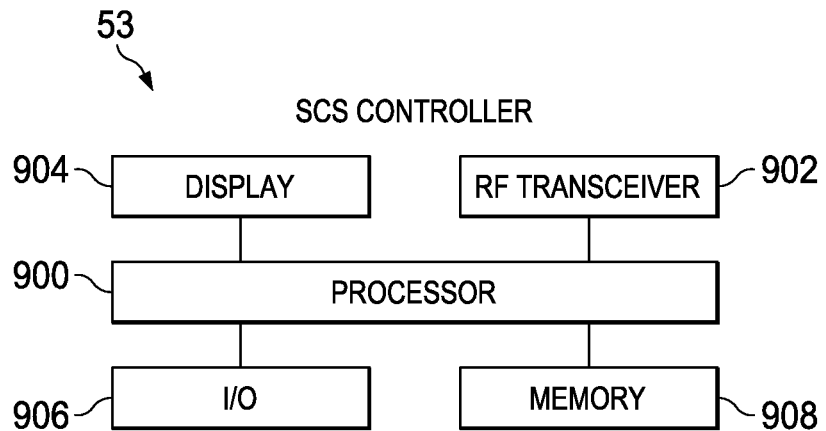
FIG. 17b is a block diagram of the components of a preferred embodiment of an SCS controller.

CPU 70 is in transcutaneous communications, via RF transceiver 71, with calibration and programming unit 54 and SCS controller 53. Referring to FIG. 17b, SCS controller 53 is shown. SCS controller 53 includes processor 900 connected to RF transceiver 902, display 904, input/output device 906, and memory 908. In the preferred embodiment, display 904 is a low power liquid crystal display adapted to show the current operational state of the system. I/O device 906 is a simple push button contact array which is constantly monitored by processor 900. Memory 908 is onboard memory connected to processor 900. In the preferred embodiment, RF transceiver 902 is a low power transmitter/receiver combination.

Figure 17C:
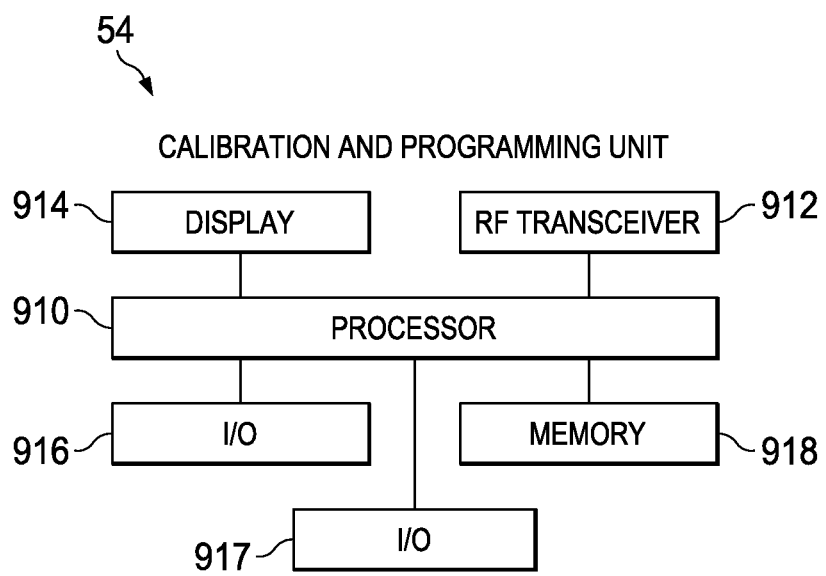
FIG. 17c is a block diagram of the components of a preferred embodiment of a calibration and programming unit.

Referring to FIG. 17c, calibration and programming unit 54 will be described. Calibration and programming unit 54 includes processor 910 connected to onboard memory 918, input/output devices 916 and 917, RF transceiver 912 and display 914. Display 914, in the preferred embodiment, is a low power liquid crystal display. Input/output device 916 and input/output device 917 are simple push button switches monitored continuously by the processor. Memory 918 is onboard processor 910. RF transceiver 912 is a low power transmitter/receiver combination.

Referring to FIGS. 18a, 18b, 18c and FIG. 17a, method 80 of operation of the positionally-sensitive spinal cord stimulator is shown. In the preferred embodiment, method 80 takes the form of a computer program which is resident in memory 72 of CPU 70 of PGSP 50. When activated, the program forms a continuous cycle.

Figure 18A:
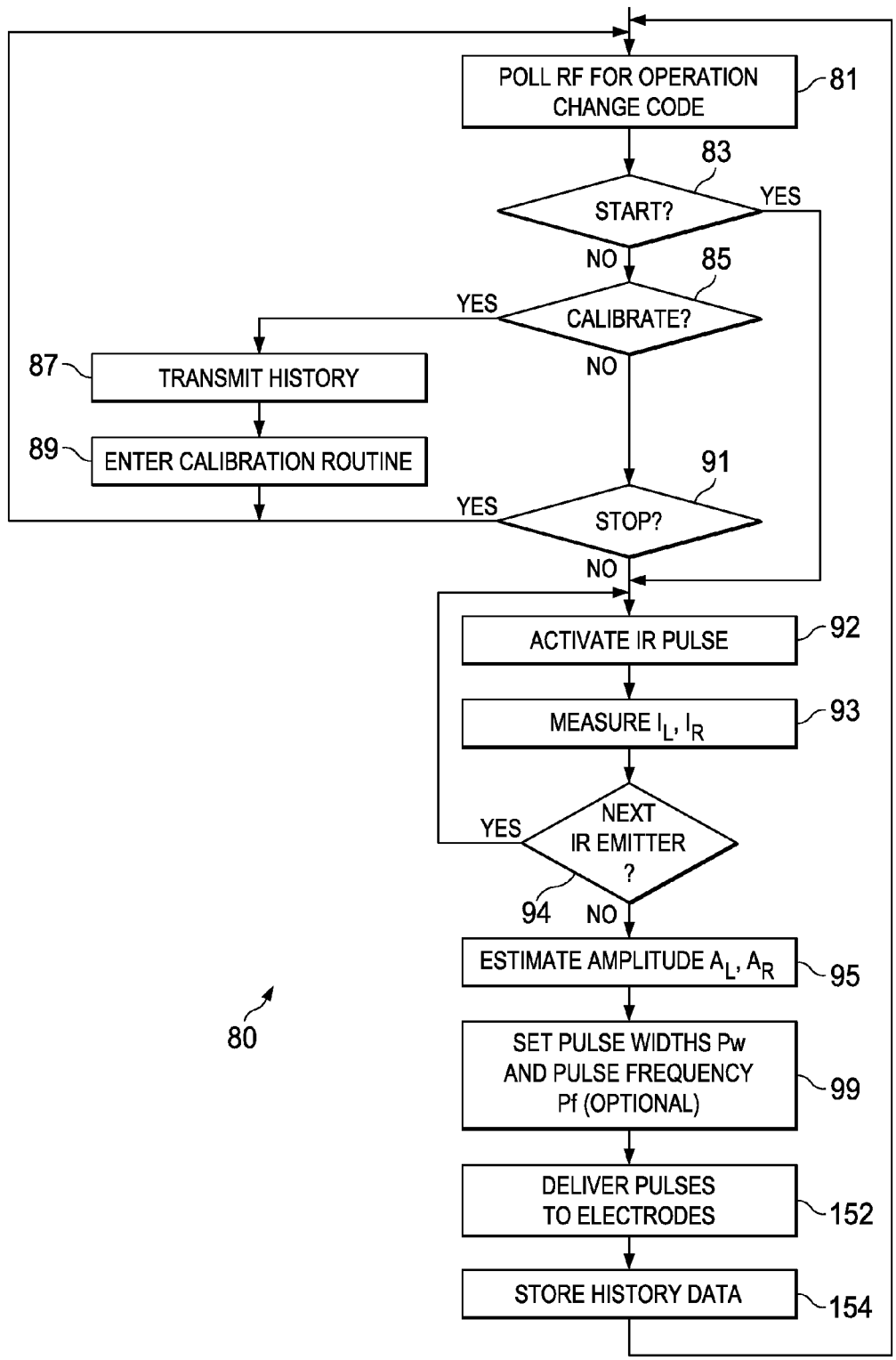
FIGS. 18a-18d are flow diagrams of a method of operation of a preferred embodiment.

Beginning with FIG. 18a, at step 81, RF transceiver 71 is continually polled for a change of operation code signal to be received from SCS controller 53. One of three options is always present, "start?", "calibrate?" and "stop?".

At step 83, if operation change code "start?" is received, the method moves to step 92. At step 92, CPU 70 activates optical modulator 68, which in turn activates IR emitter driver 66 to generate an optical pulse from a first IR emitter in the set of IR emitters. At step 93, a first pair of photocurrent levels at the photodetectors, $I_L[1]$ and $I_R[1]$, are measured by optical signal processor 64 and passed to CPU 70 for storage in memory. At step 94, if additional IR emitters are utilized then the method repeats step 92 for the second IR emitter and repeats step 93 to measure a second pair of photocurrent levels $I_L[2]$ and $I_R[2]$ and store them in memory. Steps 92, 93 and 94 are repeated for n IR emitters, storing a set of photocurrent pairs $(I_L[1],I_R[1]), (I_L[2],I_R[2]), \ldots, (I_L[n],I_R[n])$.

At step 95, CPU estimates the amplitude $A_L$ and $A_R$ of a train of pulses to be sent to the electrodes, based on the set of photocurrent pairs. At step 99, optionally, the CPU sets the values of the pulse width $P_W$ and frequency $P_f$ of the pulse train to be sent to the electrodes. At step 152, the CPU activates the pulse modulator to create the waveform of the pulse train to be sent to the electrodes and activates pulse generator 60 to generate the pulse train. At step 154, the CPU stores the values of $I_L[1], A_L[n], I_R[1], \ldots I_R[1], A_L, A_R, P_W$ and $P_f$ in memory for future retrieval. The method then returns to step 81.

If at step 83, the operation change code is not "start?", the method proceeds to step 85. At step 85, the CPU determines if the operation change code is "calibrate?". If so, the method moves to step 87. At step 87, the CPU transmits the history log stored in memory to calibration unit 54. At step 89, the CPU enters the calibration routine as will be described more fully later. The method then returns to step 81.

If at step 85, the operation change code is not "calibrate?", the method moves to step 91. At step 91, the CPU determines if the operation change code is "stop?". If so, the method returns to step 81. If not, the method proceeds to step 92 and continues as previously described.

In the preferred embodiment, the pulse width and frequency is kept constant for a given patient and only the left and right electrode amplitudes are varied. In another embodiment, step 99 is performed whereby pulse width and pulse frequency are dynamically varied according to the calibration values stored in the calibration table for each electrode.

Figure 18B:
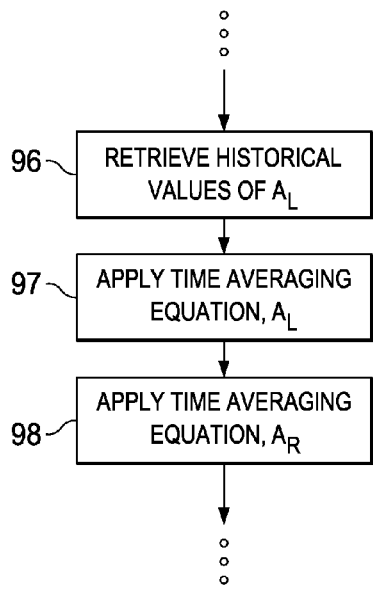

Referring to FIG. 18b, an alternate embodiment of estimating amplitude values, at step 95 is shown. In this embodiment, the CPU time averages historical amplitudes $A_L$ and $A_R$ to arrive at the estimated electrode amplitudes. At step 96, the CPU obtains a set of historical values for $A_L$ and $A_R$ and a predetermined weighting value from memory.

At step 97, the following equation is applied:

$$A_L(\text{delivered}) = \frac{w_k \cdot A_L(k) + w_{k-1} \cdot A_L(k-1) + w_{k-2} \cdot A_L(k-2) + \ldots}{w_k + w_{k-1} + w_{k-2} + \ldots} \quad (9)$$

where:

$w_k$=predetermined weight for the values of $A_L$ at the current time $A_L(k)$ and earlier times $A_L(k-1)$, $A_L(k-2), \ldots$ At time k;

$A_L$=left electrode amplitude; and,

At step 98, the following equation is applied:

$$A_R(\text{delivered}) = \frac{w_k \cdot A_R(k) + w_{k-1} \cdot A_R(k-1) + w_{k-2} \cdot A_R(k-2) + \ldots}{w_k + w_{k-1} + w_{k-2} + \ldots} \quad (10)$$

where:

$w_k$=predetermined weight for the values of $A_R$ at the current time $A_R(k)$ and earlier times $A_R(k-1)$, $A_R(k-2), \ldots$ At time k;

$A_R$=right electrode amplitude.

Figure 18C:
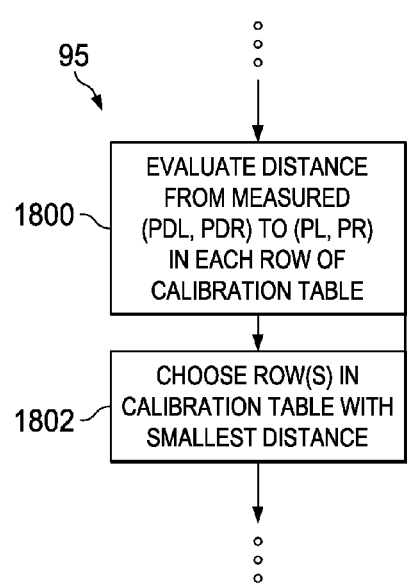

Referring to FIG. 18c, another alternate method of estimating amplitude values at step 95 is shown.

At step 1800, the CPU computes a distance factor dP according to the equation:

$$dP = \sqrt{\sum_{i,j}(PD_{ij} - I_{ij})^2} \quad (11)$$

where =measured value of jth photodetector current due to ith optical emitter, and $PD_{ij}$=calibration table value of jth photodetector current generated by ith optical emitter.

dP is calculated for each row corresponding to patient positions 1-4 of the calibration table. At step 1802, the values $A_L$ and $A_R$ are estimated as those that correspond to the row of the calibration table having the smallest distance factor dP.

Figure 18D:
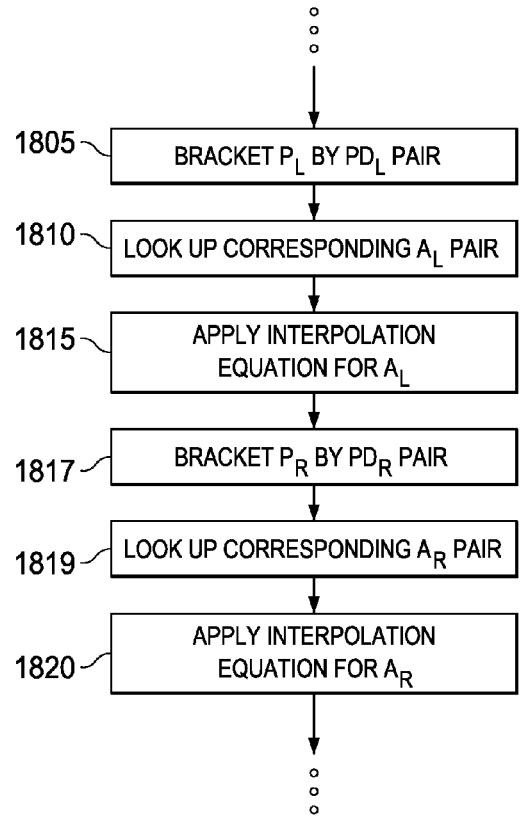

Referring to FIG. 18d, another alternate method of estimating amplitude values, step 95, is shown.

At step 1805, the CPU consults the calibration table to locate the closest pair of consecutive $PD_{iL}$ values that bracket the measured value $I_{iL}$, [$PD_{iL\ TOP}$, $PD_{iL\ BOTTOM}$]. At step 1810, the CPU locates the pair of $A_L$ values that correspond to the closest pair of $PDi_L$ values, [$A_{L\ TOP}$, $A_{L\ BOTTOM}$]. At step 1815, the CPU applies the interpolation equation to locate the estimated value of $A_L$, as follows:

$$A_L = \text{Average}\left[\left(\frac{(A_{LTOP} - A_{LBOTTOM})}{(PD_{iLTOP} - PD_{iLBOTTOM})}\right) \cdot (I_{iL} - PD_{iLBOTTOM}) + A_{LBOTTOM}\right] \quad (12)$$

where:

$A_L$=estimated value of the left electrode pulse current;

$I_{iL}$=measured value of photodetector current for the left photodetector and the ith optical emitter;

$PD_{iLTOP}$=upper bracketed value of photodetector current from the calibration table for the left photodetector and the ith optical emitter;

$PD_{iL\ BOTTOM}$=lower bracketed value of the photodetector current from the calibration table for the left photodetector and the ith optical emitter;

$A_{L\ TOP}$=upper value of the electrode pulse current from the calibration table corresponding to $PDi_{L\ TOP}$;

$A_{L\ BOTTOM}$=lower value of the pair of electrode amplitudes from the calibration table corresponding to $PDi_{L\ BOTTOM}$; and, the average is taken over all optical emitters i.

At step 1817, the CPU consults the calibration table to locate the closest pair of consecutive $PD_{iR}$ values that bracket the measured value $I_{iR}$, [$PD_{iR\ TOP}$, $PD_{iR\ BOTTOM}$]. At step 1819, the CPU locates the pair of $A_R$ values that correspond to the closest pair of $PD_{iR}$ values, [$A_{R\ TOP}$, $A_{R\ BOTTOM}$]. At step 1820, the CPU applies the interpolation equation to locate the estimated value of $A_R$, as follows:

$$A_R = \text{Average}\left[\left(\frac{(A_{RTOP} - A_{RBOTTOM})}{(PD_{iRTOP} - PD_{iRBOTTOM})}\right) \cdot (I_{iR} - PD_{iRBOTTOM}) + A_{RBOTTOM}\right] \quad (13)$$

where:

$A_R$=estimated value of the right electrode pulse current;

$I_{iR}$=measured value of photodetector current for the right photodetector and the ith optical emitter;

$PD_{iR\ TOP}$=upper bracketed value of photodetector current from the calibration table for the ith optical emitter;

$PD_{iR\ BOTTOM}$=lower bracketed value of photodetector current from the calibration table for the ith optical emitter;

$A_{R\ TOP}$=upper value of the electrode pulse current from the calibration table corresponding to $PDi_{R\ TOP}$;

$A_{R\ BOTTOM}$=lower value of the pair of electrode amplitudes from the calibration table corresponding to $PDi_{R\ BOTTOM}$; and, the average is taken over all optical emitters i.

Figure 19A:
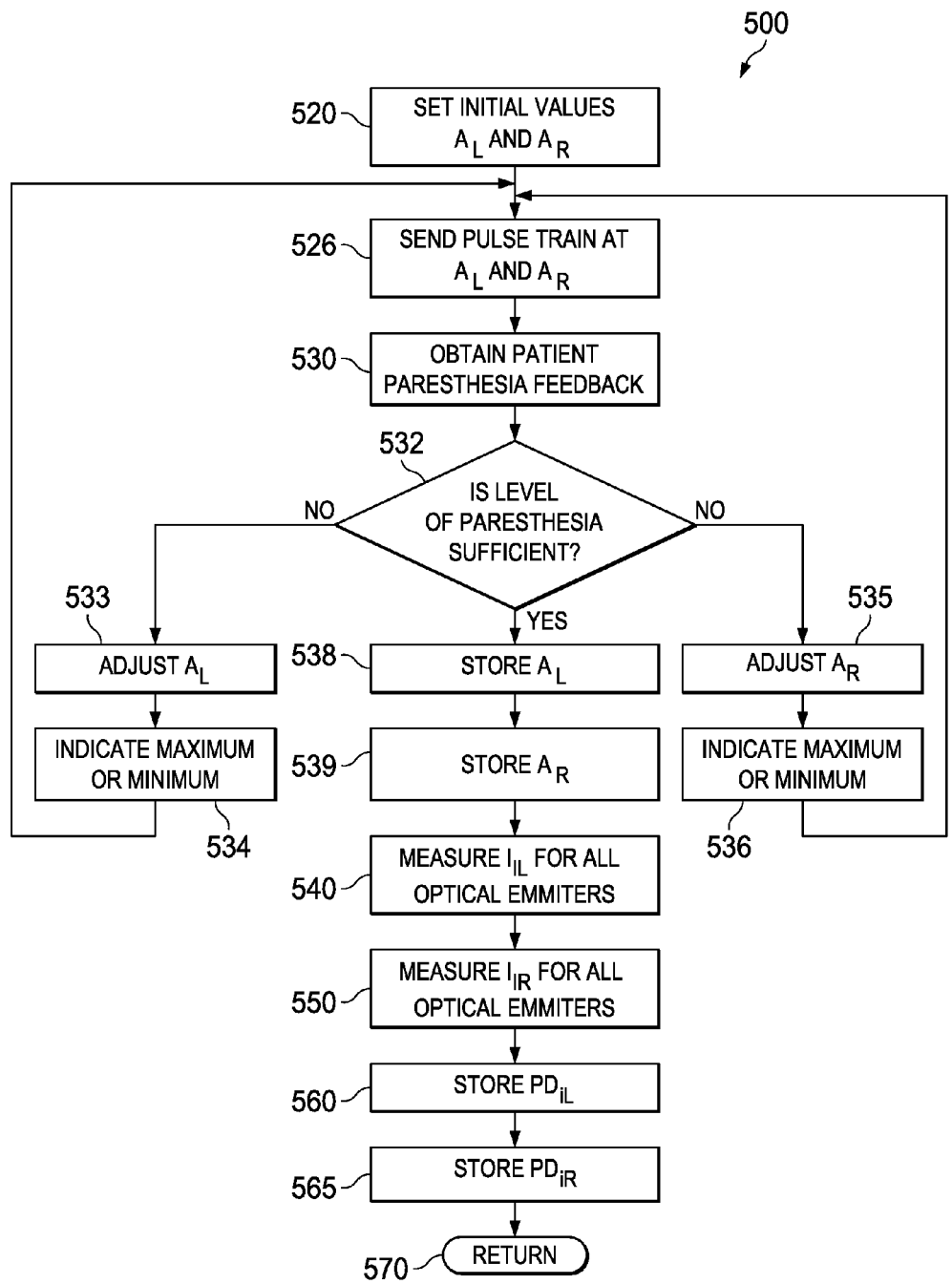
FIGS. 19a-19c are flow diagrams of a method of calibrating a preferred embodiment.

Referring to FIG. 19a, the processor is programmed to carry out steps of calibration method 500 upon request by a calibration control program. At step 520, the amplitudes $A_L$ and $A_R$ are set at the minimum value of a predetermined range. At step 525, the pulse generator is directed by the CPU to send a train of pulses to each of the left and right electrodes at the minimum levels of $A_L$ and $A_R$, respectively. At step 530, paresthesia perception feedback is solicited from the patient.

If the level of parasthesia is not optimal according to the patient feedback, then the method moves to step 532. At step 532, the processor monitors the input/output devices to determine if $A_L$, $A_R$ or both $A_L$ and $A_R$ need to be adjusted, or if the level of paresthesia is sufficient. If $A_L$ needs to be increased or decreased from the current level, then the value of $A_L$ is adjusted by a discrete amount in step 533. If the level of $A_L$ is at a maximum or a minimum level, an alert is made by the calibration and programming unit in step 534. If $A_R$ needs to be increased or decreased from the current level, then the value of $A_R$ is adjusted by a discrete amount in step 535. If the level of $A_R$ is at a maximum or a minimum level, an alert is made by the calibration and programming unit in step 536. The alert in step 534 and step 536 may be a visual indication, audio indication or both visual and audio indication.

After adjustment, the step 525 is repeated, and a train of pulses is delivered to each electrode at the new levels $A_L$ and $A_R$. At step 530, patient paresthesia feedback is again solicited. If the level of paresthesia is still not optimal according to the patient feedback, the method repeats steps 533, 534, 535 and 536 as required. If the level of paresthesia is sufficient according to patient feedback at step 532, the method moves to step 538.

At step 538, the CPU stores the value $A_L$. At step 539, the CPU stores the value of $A_R$. At step 540, the CPU measures the optical signals from the optical signal processor representative of the set of photocurrents $I_{iL}$ from the left photodetector generated by the ith optical emitter. At step 550, the CPU measures the optical signals from the optical signal processor representative of the set of photocurrents $I_{iR}$ from the right photodetector generated by the ith optical emitter. At steps 560 and 565, the CPU stores the sets of photocurrents $I_{iL}$ and $I_{iR}$ in the calibration table as calibrated values $PD_{iL}$ and $PD_{iR}$. At step 570, the calibration method steps complete by returning control to the calibration control program.

Figure 19B:
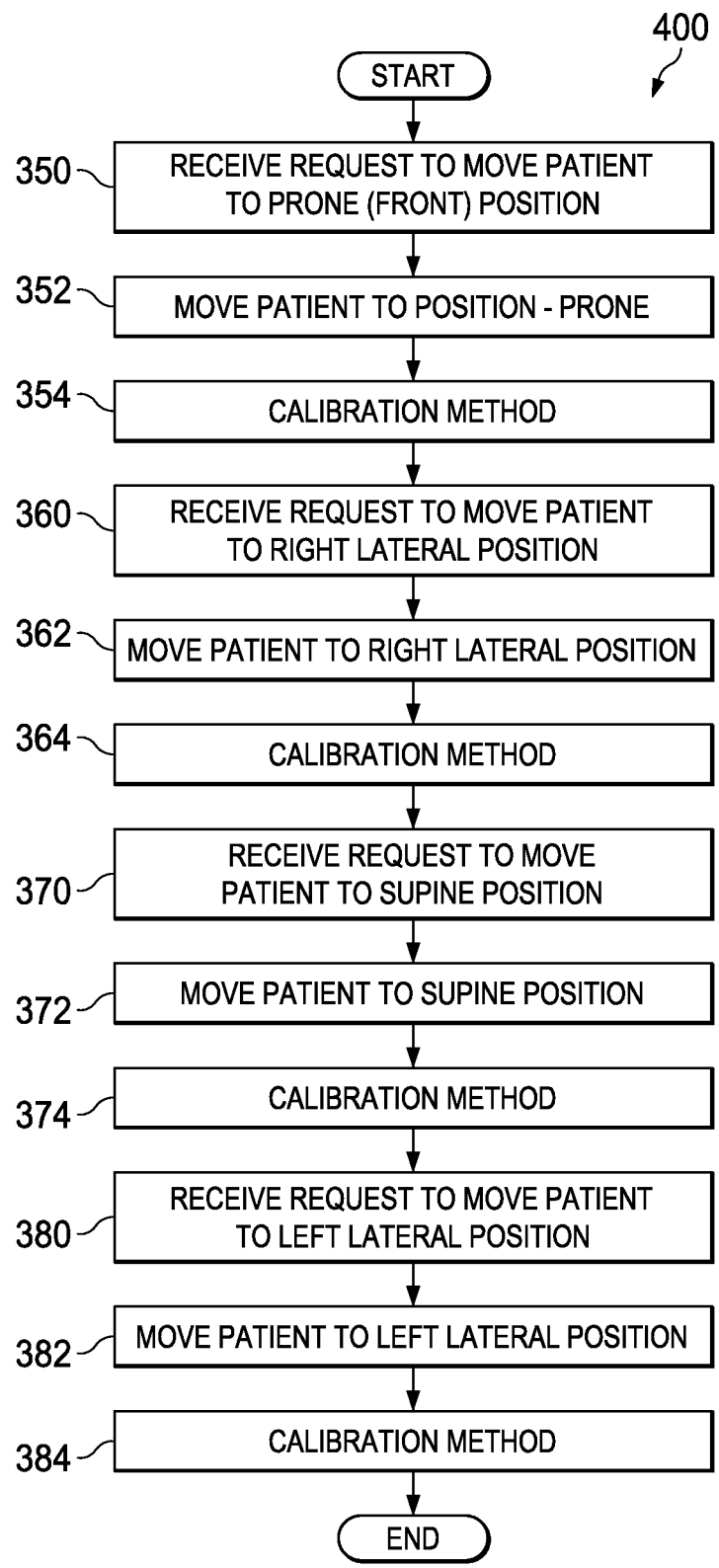

Referring to FIG. 19b, the processor of calibration unit 54 is programmed to further carry out the following method steps for a calibration control program 400 in cooperation with physical motion of the patient.

At step 350, RF transceiver 912 receives a signal indicative of a request to move the patient to a prone position and passes it to processor 910. At step 352, the patient is positioned in a prone position. At step 354, calibration method 500, as described in FIG. 19a, is carried out to maximize the level of paresthesia experienced by the patient.

At step 360, RF transceiver 912 receives a signal indicative of a request to move the patient to a right lateral position and passes it to processor 910. At step 362, the patient is positioned in a right lateral position. At step 364, calibration method 500 is then carried out to optimize the level of paresthesia experienced by the patient.

At step 370, RF transceiver 912 receives a signal indicative of a request to move the patient to a supine position and passes it to processor 910. At step 372, the patient is positioned in a supine position. At step 374, calibration method 500 is then carried out to optimize the level of paresthesia experienced by the patient.

At step 380, RF transceiver 912 receives a signal indicative of a request to move the patient to a left lateral position and passes it to processor 910. At step 382, the patient is positioned in a left lateral position. At step 384, calibration method 500 is then carried out to optimize the level of paresthesia experienced by the patient.

After steps 380, 382 and 384 are performed, the calibration program is complete.

The order of patient positions in calibration program 400 may be changed in alternative embodiments. Additional patient positions may be added to calibration program 400 in alternative embodiments, for example, the patient may be rotated clockwise to calibrate a level of paresthesia required for a clockwise position.

Figure 19C:
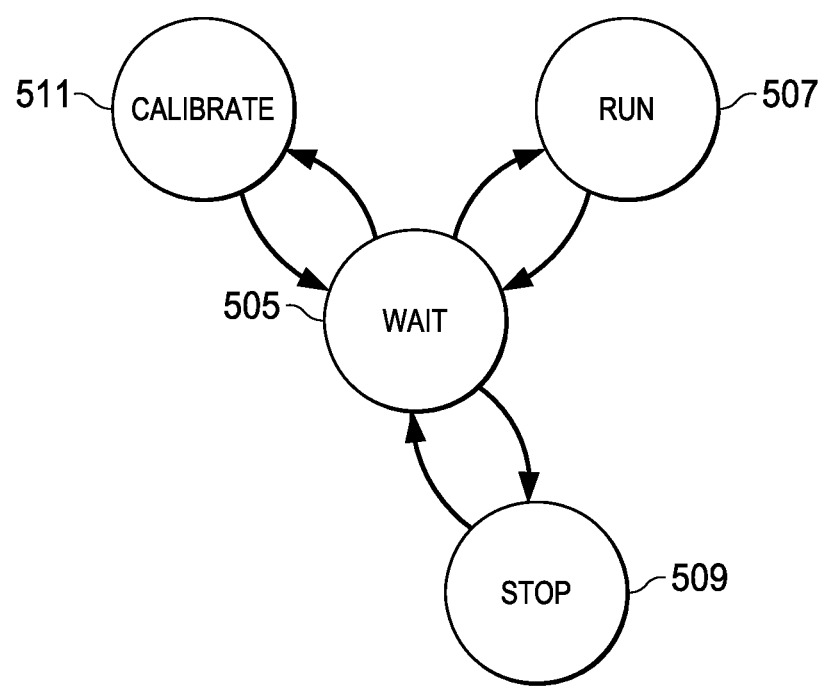

Referring to FIG. 19c, the various states of the SCS controller will be described. At wait state 505, SCS controller 53 enters a waiting posture and continually polls I/O device 906. Upon receipt, processor 900 enters run state 507 and transmits a "run" signal to RF transceiver 902. RF transceiver then transmits the "run" signal to PGSP 50 for further action. After transmission, the processor returns to wait state 505.

If a "stop" signal is received from I/O device 906, at step 509, processor 900 passes a signal to RF transceiver 902, which in turn sends the signal to PGSP 50. The processor then returns to wait state 505.

If a "calibrate" signal is received from I/O device 906, at step 511, processor 900 transmits a "calibrate" signal to RF transceiver 902, which in turn sends the signal to PGSP 50. Processor 900 then returns to wait state 505.

Figure 20:
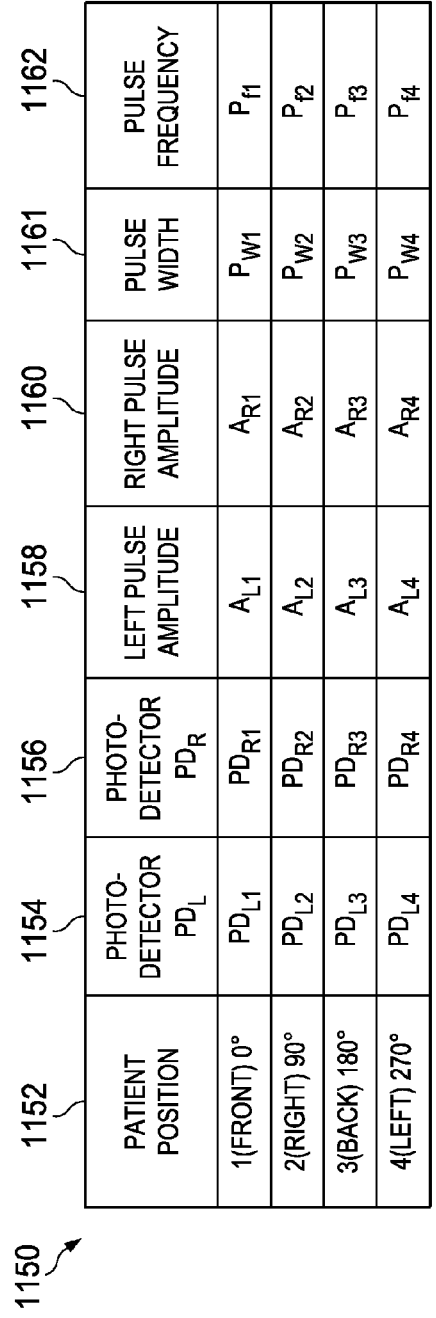
FIG. 20 is a graphic representation of a calibration table for one optical emitter and multiple optical detectors.

FIG. 20 shows a calibration table 1150 for a first embodiment suitable for the arrangement of optical emitters, optical collectors and electrodes described in FIGS. 8a-8d. Each row is a record for the optimal electrode settings for a patient position for a specific pair of electrodes in the electrode assembly. Calibration table 1150 includes seven columns, patient position identifier 1152, left photodetector current value $PD_L$ 1154, right photodetector current value $PD_R$ 1156, left electrode stimulation pulse amplitude $A_L$ 1158, right electrode pulse amplitude $A_R$ 1160, electrode stimulation pulse width $P_W$ 1161, and electrode pulse frequency $P_f$ 1162.

Patient position identifier 1152 in a preferred embodiment includes four positions, front (prone-0°), right-90°, back (supine-180°) and left-270°. Each row in Table 1150 is associated with one of the four patient positions. Left electrode stimulation pulse amplitude 1158 and right electrode stimulation pulse amplitude 1160 are values which are derived during calibration and recorded for different spinal cord positions, corresponding to the patient position. In the preferred embodiment, the left electrode stimulation pulse amplitude 1158 and right electrode stimulation pulse amplitude 1160 are directly proportional to the stimulation energy delivered to the respective electrodes.

In alternate embodiments, calibration may be performed for additional physical positions such that additional rows are placed in table 1150.

Electrode stimulation pulse width 1161 and frequency 1162 are shown as having constant values. However, in an alternate embodiment, the values of electrode stimulation pulse width 1161 and electrode pulse frequency 1162 are varied through a predetermined range during calibration and recorded for each patient position using interpolation means, such as those shown for pulse amplitude, to adjust the values while in operation.

Figure 21:
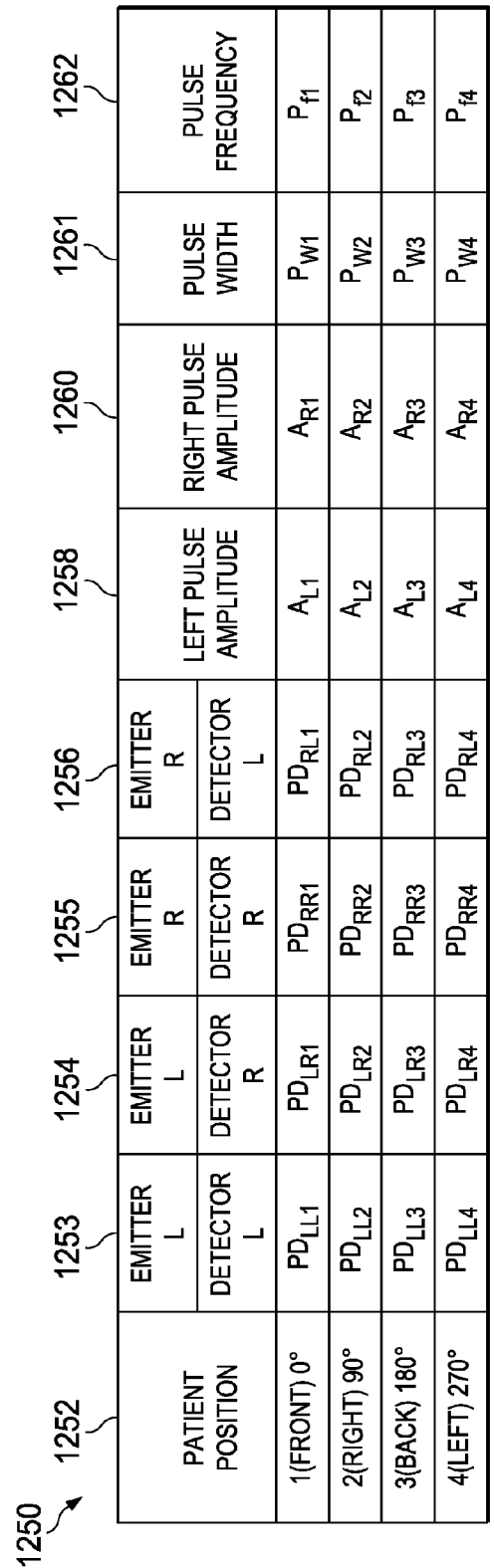
FIG. 21 is a graphic representation of a calibration table for multiple optical emitters and multiple optical detectors.

FIG. 21 shows a calibration table 1250 for a second embodiment suitable for the arrangement of optical emitters, optical collectors and electrodes described in FIGS. 10a-10d. Each row is a record for the optimal electrode settings for a patient position for a specific pair of electrodes in the electrode assembly. Calibration table 1250 includes nine columns, patient position identifier 1252, left photodetector value $PD_{LL}$ 1253 for light detected from the left optical emitter, right photodetector value $PD_{LR}$ 1254 for light detected from the left optical emitter, right photodetector value $PD_{RR}$ 1255 for light detected from the right optical emitter, right photodetector value $PD_{RL}$ 1256 for light detected from the right optical emitter, left electrode stimulation pulse amplitude $A_L$ 1258, right electrode pulse amplitude $A_R$ 1260, electrode stimulation pulse width $P_W$ 1261, and electrode pulse frequency $P_f$ 1262.

Patient position identifier 1252 in a preferred embodiment includes four positions, front (prone-0°), right-90°, back (supine-180°) and left-270°. Each row in Table 1250 is associated with one of the four patient positions. Left electrode stimulation pulse amplitude 1258 and right electrode stimulation pulse amplitude 1260 are values which are derived during calibration and recorded for different spinal cord positions, corresponding to the patient position. In the preferred embodiment, the left electrode stimulation pulse amplitude 1258 and right electrode stimulation pulse amplitude 1260 are directly proportional to the stimulation energy delivered to the respective electrodes.

In alternate embodiments, calibration may be performed for additional physical positions such that additional rows are placed in table 1250.

Electrode stimulation pulse width 1261 and frequency 1262 are shown as having constant values. However, in an alternate embodiment, the values of electrode stimulation pulse width 1261 and electrode pulse frequency 1262 are varied through a predetermined range during calibration and recorded for each patient position. Interpolation may be used to determine the pulse width and frequency, such as those shown for pulse amplitude, to adjust the values while in operation.

The disclosure of Table 1250 is not intended to limit the invention, but show an example of multiple optical detectors with multiple optical emitters. Other calibration tables can be generated in a similar manner for more than two optical detectors and two optical emitters.

The disclosure demonstrates a novel optical sensor, generally useful in many fields of endeavor, in which a probe light beam is emitted from the sensor and a responsive light beam is collected by the sensor, where the sensor comprises a negative axicon element coupled to an optical fiber. In a preferred embodiment, the negative axicon is embedded in the end of the optical fiber.

The optical fiber is further coupled to an active optical element which can be an optical emitter or an optical detector. In a preferred embodiment, both an optical emitter and an optical detector are coupled to a single optical fiber with the negative axicon using an optical circulator. In an alternate embodiment, a set of optical fibers coupled to a set of negative axicons for emitting and detecting light are conceived.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed and limited only by the scope and spirit of the claims now appended hereto.

The invention claimed is:

1. A stimulator system comprising:
a controller;
a set of optical emitters operatively connected to the controller, generating a set of incident light beams to a surface;
a set of optical detectors operatively connected to the controller, receiving a set of reflected light beams from the surface;
a set of optical elements, operatively coupled to the set of optical emitters and to the set of optical detectors, emitting the set of incident light beams and collecting the set of reflected light beams;
a set of electrodes operatively connected to the controller;
wherein the controller generates a position of the surface from the set of reflected light beams;
the controller directing a set of currents to the set of electrodes based on the surface position; and,
wherein each optical element of the set of optical elements both emits one of the set of incident light beams and collects one of the set of reflected light beams.

2. The system of claim 1 further comprising:
an optical fiber, coupled to an optical emitter in the set of optical emitters, an optical detector in the set of optical detectors, and, an optical element in the set of optical elements.

3. The system of claim 2 wherein the set of electrodes are positioned adjacent the set of optical elements.

4. The system of claim 2 further comprising an implantable lead encasing the optical fiber and a lumen.

5. The system of claim 4 wherein the implantable lead further comprises an EMI shield.

6. The system of claim 5 wherein the EMI shield further comprises carbon nanotubes.

7. The system of claim 2 further comprising an optical circulator operatively coupled to the optical emitter, the optical detector and the optical fiber.

8. The system of claim 1 wherein an optical element in the set of optical elements further comprises a negative axicon.

9. The system of claim 8 wherein the negative axicon subtends an angle less than twice the complement of the critical angle for the light incident light beams.

10. The system of claim 8 further comprising a reflective surface adjacent the negative axicon.

11. The system of claim 1 wherein an optical element in the set of optical elements further comprises a beveled surface.

12. The system of claim 11 wherein the beveled surface further comprises a reflective surface positioned at an angle less than the complement of the critical angle for incident light beams.

13. The system of claim 11 further comprising a reflective surface adjacent the beveled surface.

14. The system of claim 1 wherein an optical element in the set of optical elements further comprises a lens.

15. The system of claim 1 wherein the controller provides a set of calibrated current amplitudes and calculates an interpolation of the set of calibrated current amplitudes, and wherein the controller derives a set of current amplitudes for the set of currents based on the interpolation of the set of calibrated current amplitudes.

16. The system of claim 1 wherein the controller derives a set of current amplitudes for the set of currents based on a time averaging of a set of historical current amplitudes.

17. The system of claim 1 wherein the controller derives a set of current pulse widths for the set of currents based on at least one of the group consisting of a time averaging a set of current pulse widths, a time averaging a set of current amplitudes, an interpolation of the set of current pulse widths and an interpolation of the set of current amplitudes.

18. The system of claim 1 wherein the controller derives a set of current pulse frequencies for the set of currents based on at least one of the group consisting of a time averaging a set of current pulse frequencies, a time averaging a set of current amplitudes, an interpolation of the set of current pulse frequencies and an interpolation of the set of current amplitudes.

19. The system of claim 1 further comprising a calibration unit, operatively connected to the controller, for adjusting the set of currents.

* * * * *